US011986229B2

(12) United States Patent
Wiersdorf et al.

(10) Patent No.: US 11,986,229 B2
(45) Date of Patent: May 21, 2024

(54) OSTEOTOME WITH INFLATABLE PORTION AND MULTIWIRE ARTICULATION

(71) Applicant: Merit Medical Systems, Inc., South Jordan, UT (US)

(72) Inventors: Jason Wiersdorf, West Jordan, UT (US); Aaron Hopkinson, Herriman, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 345 days.

(21) Appl. No.: 17/024,448

(22) Filed: Sep. 17, 2020

(65) Prior Publication Data

US 2021/0077170 A1  Mar. 18, 2021

Related U.S. Application Data

(60) Provisional application No. 62/902,144, filed on Sep. 18, 2019.

(51) Int. Cl.
*A61B 17/88* (2006.01)
*A61B 17/16* (2006.01)
*A61B 17/00* (2006.01)

(52) U.S. Cl.
CPC ...... *A61B 17/8855* (2013.01); *A61B 17/1671* (2013.01); *A61B 2017/00557* (2013.01)

(58) Field of Classification Search
CPC ..... A61B 17/88; A61B 17/8855; A61B 17/16; A61B 17/1671
See application file for complete search history.

(56) References Cited

U.S. PATENT DOCUMENTS

| 2,688,329 A | 9/1954 | Wallace |
| 3,140,623 A | 7/1964 | Hoose |
| 3,228,400 A | 1/1966 | Armao |
| 3,503,385 A | 3/1970 | Stevens |
| 3,625,200 A | 12/1971 | Muller |
| 3,664,344 A | 5/1972 | Bryne |
| 3,794,039 A | 2/1974 | Kollner et al. |
| 3,908,637 A | 9/1975 | Doroshow |
| 4,033,331 A | 7/1977 | Guss et al. |
| 4,131,597 A | 12/1978 | Bluethgen et al. |
| 4,236,520 A | 12/1980 | Anderson |

(Continued)

FOREIGN PATENT DOCUMENTS

| CA | 2785207 | 7/2011 |
| CN | 88203061 | 11/1988 |

(Continued)

OTHER PUBLICATIONS

US 7,063,700 B2, 06/2006, Michelson (withdrawn)

(Continued)

*Primary Examiner* — Christopher J Beccia
(74) *Attorney, Agent, or Firm* — Dorsey & Whitney LLP

(57) ABSTRACT

Devices used to treat tissue, including treatment of vertebral bone fractures, are disclosed. The devices may be configured to displace bone tissue using an expandable member, such as a balloon. The devices may further include a handle having a rotatable grip configured to apply a tension force to a plurality of pull wires to articulate a distal portion of the devices.

22 Claims, 15 Drawing Sheets

(56) References Cited

U.S. PATENT DOCUMENTS

| | | |
|---|---|---|
| 4,276,880 A | 7/1981 | Malmin |
| 4,294,251 A | 10/1981 | Grennwald et al. |
| 4,337,773 A | 7/1982 | Raftopoulos et al. |
| 4,386,717 A | 6/1983 | Koob |
| 4,399,814 A | 8/1983 | Pratt, Jr. et al. |
| 4,411,266 A | 10/1983 | Cosman |
| 4,456,017 A | 6/1984 | Miles |
| 4,473,077 A | 9/1984 | Noiles |
| 4,476,861 A | 10/1984 | Dimakos et al. |
| 4,578,061 A | 3/1986 | Lemelson |
| 4,586,923 A | 5/1986 | Gould et al. |
| 4,595,006 A | 6/1986 | Burke et al. |
| 4,619,263 A | 10/1986 | Frisbie et al. |
| 4,627,434 A | 12/1986 | Murray |
| 4,641,654 A | 2/1987 | Samson et al. |
| 4,653,489 A | 3/1987 | Tronzo |
| 4,668,295 A | 5/1987 | Bajpai |
| 4,719,968 A | 1/1988 | Speros |
| 4,722,948 A | 2/1988 | Sanderson |
| 4,731,054 A | 3/1988 | Billeter et al. |
| 4,742,817 A | 5/1988 | Kawashima et al. |
| 4,747,840 A | 5/1988 | Ladika et al. |
| 4,748,969 A | 6/1988 | Wardle |
| 4,784,638 A | 11/1988 | Ghajar et al. |
| 4,795,602 A | 1/1989 | Pretchel et al. |
| 4,842,603 A | 6/1989 | Draenert |
| 4,843,112 A | 6/1989 | Gerhart et al. |
| 4,846,814 A | 7/1989 | Ruiz |
| 4,865,586 A | 9/1989 | Hedberg |
| 4,869,906 A | 9/1989 | Dingeldein et al. |
| 4,888,366 A | 12/1989 | Chu et al. |
| 4,900,303 A | 2/1990 | Lemelson |
| 4,961,730 A | 10/1990 | Bodicky et al. |
| 4,961,731 A | 10/1990 | Poncy |
| 4,963,151 A | 10/1990 | Ducheyene et al. |
| 4,969,870 A | 11/1990 | Kramer et al. |
| 4,969,888 A | 11/1990 | Scholten et al. |
| 4,982,730 A | 1/1991 | Royce |
| 4,998,923 A | 3/1991 | Samson et al. |
| 5,004,501 A | 4/1991 | Faccioli |
| 5,017,627 A | 5/1991 | Bonfield |
| 5,046,513 A | 9/1991 | O'Leary et al. |
| 5,049,137 A | 9/1991 | Thompson |
| 5,049,157 A | 9/1991 | Mittelmeier et al. |
| 5,059,193 A | 10/1991 | Kuslich |
| 5,085,861 A | 2/1992 | Gerhart et al. |
| 5,088,991 A | 2/1992 | Weldon |
| 5,092,891 A | 3/1992 | Kummer et al. |
| 5,103,804 A | 4/1992 | Abele |
| 5,108,404 A | 4/1992 | Scholten et al. |
| 5,112,303 A | 5/1992 | Pudenz et al. |
| 5,114,414 A | 5/1992 | Buchbinder |
| 5,116,305 A | 5/1992 | Milder et al. |
| 5,147,334 A | 9/1992 | Moss |
| 5,156,606 A | 10/1992 | Chin |
| 5,163,431 A | 11/1992 | Greip |
| 5,184,757 A | 2/1993 | Giannuzzi |
| 5,188,619 A | 2/1993 | Myers |
| 5,196,201 A | 3/1993 | Larsson et al. |
| 5,197,971 A | 3/1993 | Bonutti |
| 5,211,631 A | 5/1993 | Sheaff |
| 5,231,989 A | 8/1993 | Middleman et al. |
| 5,242,082 A | 9/1993 | Giannuzzi |
| 5,264,214 A | 11/1993 | Rhee et al. |
| 5,266,248 A | 11/1993 | Ohtsuka et al. |
| 5,269,750 A | 12/1993 | Grulke et al. |
| 5,282,821 A | 2/1994 | Donahue |
| 5,284,128 A | 2/1994 | Hart |
| 5,285,795 A | 2/1994 | Ryan et al. |
| 5,295,980 A | 3/1994 | Ersek |
| 5,296,026 A | 3/1994 | Monroe et al. |
| 5,308,342 A | 5/1994 | Sepetka et al. |
| 5,322,064 A | 6/1994 | Lundquist |
| 5,322,505 A | 6/1994 | Krause et al. |
| 5,334,181 A | 8/1994 | Rubinsky et al. |
| 5,336,699 A | 8/1994 | Cooke et al. |
| 5,343,877 A | 9/1994 | Park |
| 5,352,715 A | 10/1994 | Wallace et al. |
| 5,356,629 A | 10/1994 | Sander |
| 5,360,416 A | 11/1994 | Ausherman et al. |
| 5,368,598 A | 11/1994 | Hasson |
| 5,372,587 A * | 12/1994 | Hammerslag ...... A61M 25/0144 604/95.04 |
| 5,378,234 A | 1/1995 | Hammerslag et al. |
| 5,380,307 A | 1/1995 | Chee et al. |
| 5,385,563 A | 1/1995 | Gross |
| 5,389,073 A | 2/1995 | Imran |
| 5,425,770 A | 6/1995 | Piez et al. |
| 5,431,168 A | 7/1995 | Webster, Jr. |
| 5,431,639 A | 7/1995 | Shaw |
| 5,437,636 A | 8/1995 | Snoke et al. |
| 5,449,301 A | 9/1995 | Hanna et al. |
| 5,449,351 A | 9/1995 | Zohmann |
| 5,458,597 A | 10/1995 | Edwards et al. |
| 5,480,382 A | 1/1996 | Hammerslag et al. |
| 5,484,424 A | 1/1996 | Cottenceau et al. |
| 5,489,275 A | 2/1996 | Thompson et al. |
| 5,496,330 A | 3/1996 | Bates et al. |
| 5,512,610 A | 4/1996 | Lin |
| 5,514,130 A | 5/1996 | Baker |
| 5,514,137 A | 5/1996 | Coutts |
| 5,531,715 A | 7/1996 | Engelson et al. |
| 5,535,922 A | 7/1996 | Maziarz |
| 5,549,542 A | 8/1996 | Kovalcheck |
| 5,549,679 A | 8/1996 | Kuslich |
| 5,554,114 A | 9/1996 | Wallace et al. |
| 5,571,085 A | 11/1996 | Accisano, III |
| 5,571,088 A | 11/1996 | Lennox |
| 5,574,075 A | 11/1996 | Draemert |
| 5,599,346 A | 2/1997 | Edwards et al. |
| 5,616,121 A | 4/1997 | McKay |
| 5,620,447 A | 4/1997 | Smith et al. |
| 5,620,467 A | 4/1997 | Wagner |
| 5,624,396 A | 4/1997 | McNamara et al. |
| 5,628,771 A | 5/1997 | Mizukawa et al. |
| 5,637,090 A | 6/1997 | McGee |
| 5,637,091 A | 6/1997 | Hakky et al. |
| 5,662,680 A | 9/1997 | Desai |
| 5,681,282 A | 10/1997 | Eggers et al. |
| 5,681,289 A | 10/1997 | Wilcox et al. |
| 5,681,317 A | 10/1997 | Caldarise |
| 5,685,826 A | 11/1997 | Bonutti |
| 5,695,513 A | 12/1997 | Johnson et al. |
| 5,697,536 A | 12/1997 | Eggers et al. |
| 5,697,909 A | 12/1997 | Eggers et al. |
| 5,700,157 A | 12/1997 | Chung |
| 5,704,926 A | 1/1998 | Sutton |
| 5,709,697 A | 1/1998 | Ratcliff et al. |
| 5,725,568 A | 3/1998 | Hastings |
| 5,735,829 A | 4/1998 | Cherian |
| 5,741,320 A | 4/1998 | Thornton et al. |
| 5,766,153 A | 6/1998 | Eggers et al. |
| 5,800,408 A | 9/1998 | Strauss et al. |
| 5,810,804 A | 9/1998 | Gough |
| 5,810,867 A | 9/1998 | Zarbateny et al. |
| 5,820,592 A | 10/1998 | Hammerslag et al. |
| 5,833,632 A | 11/1998 | Jacobsen et al. |
| 5,833,692 A | 11/1998 | Cesarini et al. |
| 5,847,046 A | 12/1998 | Jiang et al. |
| 5,849,028 A | 12/1998 | Chen |
| 5,851,212 A | 12/1998 | Zirps et al. |
| 5,855,577 A | 1/1999 | Murphy-Chutorian et al. |
| 5,858,003 A | 1/1999 | Atala |
| 5,860,952 A | 1/1999 | Quinn |
| 5,860,974 A | 1/1999 | Abele |
| 5,876,373 A | 3/1999 | Giba et al. |
| 5,891,027 A | 4/1999 | Tu |
| 5,902,251 A | 5/1999 | Vanhooydonk |
| 5,902,839 A | 5/1999 | Lautenschlager et al. |
| 5,914,356 A | 6/1999 | Erbe |
| 5,921,956 A | 7/1999 | Grinberg et al. |
| 5,928,239 A | 7/1999 | Mirza |
| 5,931,829 A | 8/1999 | Burbank et al. |
| 5,944,715 A | 8/1999 | Goble et al. |

(56) References Cited

U.S. PATENT DOCUMENTS

| | | |
|---|---|---|
| 5,947,964 A | 9/1999 | Eggers |
| 5,972,015 A | 10/1999 | Scribner et al. |
| 5,997,581 A | 12/1999 | Khalili |
| 6,019,765 A | 2/2000 | Thornhill et al. |
| 6,027,487 A | 2/2000 | Crocker |
| 6,030,360 A | 2/2000 | Biggs |
| 6,048,346 A | 4/2000 | Reiley et al. |
| 6,059,739 A | 5/2000 | Baumann |
| 6,063,078 A | 5/2000 | Wittkampf |
| 6,064,902 A | 5/2000 | Haissaguerre |
| 6,066,154 A | 5/2000 | Reiley et al. |
| 6,066,176 A | 5/2000 | Oshida |
| 6,073,051 A | 6/2000 | Sharkey et al. |
| 6,080,801 A | 6/2000 | Draenert et al. |
| 6,099,514 A | 8/2000 | Sharkey et al. |
| 6,106,524 A | 8/2000 | Eggers et al. |
| 6,106,539 A | 8/2000 | Fortier |
| 6,110,155 A | 8/2000 | Baudino |
| 6,123,702 A | 9/2000 | Swanson |
| 6,127,597 A | 10/2000 | Beyar et al. |
| 6,135,999 A | 10/2000 | Fanton et al. |
| 6,146,355 A | 11/2000 | Biggs |
| 6,156,254 A | 12/2000 | Andrews et al. |
| 6,183,435 B1 | 2/2001 | Bumbalough et al. |
| 6,203,507 B1 | 3/2001 | Wadsworth et al. |
| 6,203,574 B1 | 3/2001 | Kawamura |
| 6,228,052 B1 | 5/2001 | Pohndorf |
| 6,228,904 B1 | 5/2001 | Yadav et al. |
| 6,231,569 B1 | 5/2001 | Bek et al. |
| 6,231,615 B1 | 5/2001 | Preissman |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,251,092 B1 | 6/2001 | Qin et al. |
| 6,258,086 B1 | 7/2001 | Ashley et al. |
| 6,270,476 B1 | 8/2001 | Santoianni et al. |
| 6,280,413 B1 | 8/2001 | Clark et al. |
| 6,280,434 B1 | 8/2001 | Kinoshita et al. |
| 6,280,441 B1 | 8/2001 | Ryan |
| 6,280,456 B1 | 8/2001 | Scribner et al. |
| 6,280,473 B1 | 8/2001 | Lemperle et al. |
| 6,283,960 B1 | 9/2001 | Ashley |
| 6,291,547 B1 | 9/2001 | Lyles |
| 6,312,428 B1 | 11/2001 | Eggers |
| 6,312,454 B1 | 11/2001 | Stockel et al. |
| 6,332,894 B1 | 12/2001 | Stalcup et al. |
| 6,348,055 B1 | 2/2002 | Preissman |
| 6,352,533 B1 | 3/2002 | Ellman et al. |
| 6,358,251 B1 | 3/2002 | Mirza |
| 6,375,659 B1 | 4/2002 | Erbe et al. |
| 6,383,188 B2 | 5/2002 | Kuslich et al. |
| 6,383,190 B1 | 5/2002 | Preissman |
| 6,395,007 B1 | 5/2002 | Bhatnagar et al. |
| 6,408,889 B1 | 6/2002 | Komachi |
| 6,409,722 B1 | 6/2002 | Hoey et al. |
| 6,428,894 B1 | 8/2002 | Babich et al. |
| 6,437,019 B1 | 8/2002 | Rusin et al. |
| 6,440,138 B1 | 8/2002 | Reiley et al. |
| 6,447,506 B1 | 9/2002 | Swanson et al. |
| 6,447,514 B1 | 9/2002 | Stalcup et al. |
| 6,464,683 B1 | 10/2002 | Samuelson et al. |
| 6,478,793 B1 | 11/2002 | Cosman et al. |
| 6,479,565 B1 | 11/2002 | Stanley |
| 6,484,904 B1 | 11/2002 | Horner et al. |
| 6,506,217 B1 | 1/2003 | Arnett |
| 6,511,471 B2 | 1/2003 | Rosenman et al. |
| 6,524,296 B1 | 2/2003 | Beals |
| 6,565,588 B1 | 5/2003 | Clement et al. |
| 6,575,969 B1 | 6/2003 | Rittman et al. |
| 6,575,978 B2 | 6/2003 | Peterson et al. |
| 6,576,249 B1 | 6/2003 | Gendler et al. |
| 6,582,446 B1 | 6/2003 | Marchosky |
| 6,592,559 B1 | 7/2003 | Pakter et al. |
| 6,599,961 B1 | 7/2003 | Pienkowski et al. |
| 6,602,248 B1 | 8/2003 | Sharps et al. |
| 6,607,496 B1 * | 8/2003 | Poor .................. A61M 25/005 600/585 |
| 6,607,544 B1 | 8/2003 | Boucher et al. |
| 6,613,054 B2 | 9/2003 | Scribner et al. |
| 6,620,162 B2 | 9/2003 | Kuslich et al. |
| 6,622,731 B2 | 9/2003 | Daniel et al. |
| 6,623,448 B2 | 9/2003 | Slater |
| 6,638,268 B2 | 10/2003 | Naizi |
| 6,641,587 B2 | 11/2003 | Scribner et al. |
| 6,645,213 B2 | 11/2003 | Sand et al. |
| 6,663,647 B2 | 12/2003 | Reiley et al. |
| 6,676,665 B2 | 1/2004 | Foley et al. |
| 6,679,886 B2 | 1/2004 | Weikel et al. |
| 6,689,823 B1 | 2/2004 | Bellare et al. |
| 6,692,532 B1 | 2/2004 | Healy et al. |
| 6,716,216 B1 | 4/2004 | Boucher et al. |
| 6,719,761 B1 | 4/2004 | Reiley et al. |
| 6,719,773 B1 | 4/2004 | Boucher et al. |
| 6,726,691 B2 | 4/2004 | Osorio et al. |
| 6,730,095 B2 | 5/2004 | Olson, Jr. et al. |
| 6,740,090 B1 | 5/2004 | Cragg et al. |
| 6,740,093 B2 | 5/2004 | Hochschuler et al. |
| 6,743,239 B1 | 6/2004 | Kuehn et al. |
| 6,746,451 B2 | 6/2004 | Middleton et al. |
| 6,752,863 B2 | 6/2004 | Lyles et al. |
| 6,753,007 B2 | 6/2004 | Haggard et al. |
| 6,770,079 B2 | 8/2004 | Bhatnagar et al. |
| 6,814,734 B2 | 11/2004 | Chappuis et al. |
| 6,814,736 B2 | 11/2004 | Reiley et al. |
| 6,818,001 B2 | 11/2004 | Wulfman et al. |
| 6,832,984 B2 | 12/2004 | Stelzer et al. |
| 6,835,193 B2 | 12/2004 | Epstein et al. |
| 6,837,867 B2 | 1/2005 | Kortelling |
| 6,863,672 B2 | 3/2005 | Reiley et al. |
| 6,869,430 B2 | 3/2005 | Balbierz et al. |
| 6,869,445 B1 | 3/2005 | Johnson |
| 6,875,219 B2 | 4/2005 | Arramon |
| 6,881,214 B2 | 4/2005 | Cosman et al. |
| 6,887,246 B2 | 5/2005 | Bhatnagar et al. |
| 6,899,715 B1 | 5/2005 | Beaty |
| 6,899,719 B2 | 5/2005 | Reiley et al. |
| 6,907,884 B2 | 6/2005 | Pellegrino et al. |
| 6,913,594 B2 | 7/2005 | Coleman et al. |
| 6,916,306 B1 | 7/2005 | Jenkins et al. |
| 6,923,813 B2 | 8/2005 | Phillips |
| 6,945,956 B2 | 9/2005 | Waldhauser et al. |
| 6,953,594 B2 | 10/2005 | Lee et al. |
| 6,955,716 B2 | 10/2005 | Xu et al. |
| 6,976,987 B2 | 12/2005 | Flores |
| 6,979,312 B2 | 12/2005 | Shimada |
| 6,979,352 B2 | 12/2005 | Reynolds |
| 6,981,981 B2 | 1/2006 | Reiley et al. |
| 6,991,616 B2 | 1/2006 | Bencini et al. |
| 6,998,128 B2 | 2/2006 | Haggard et al. |
| 7,004,930 B2 | 2/2006 | Marshall |
| 7,004,945 B2 | 2/2006 | Boyd et al. |
| 7,008,433 B2 | 3/2006 | Voellmicke et al. |
| 7,018,460 B2 | 3/2006 | Xu et al. |
| 7,022,133 B2 | 4/2006 | Yee et al. |
| 7,029,468 B2 | 4/2006 | Honebrink |
| 7,044,954 B2 | 5/2006 | Reiley et al. |
| 7,059,330 B1 | 6/2006 | Makower et al. |
| 7,063,682 B1 | 6/2006 | Whayne et al. |
| 7,066,942 B2 | 6/2006 | Treace |
| RE39,196 E | 7/2006 | Ying et al. |
| 7,081,122 B1 | 7/2006 | Reiley et al. |
| 7,081,161 B2 | 7/2006 | Genge et al. |
| 7,091,258 B2 | 8/2006 | Neubert et al. |
| 7,091,260 B2 | 8/2006 | Kühn |
| 7,094,202 B2 | 8/2006 | Nobis et al. |
| 7,094,286 B2 | 8/2006 | Liu |
| 7,108,696 B2 | 9/2006 | Daniel et al. |
| 7,109,254 B2 | 9/2006 | Müller et al. |
| 7,112,205 B2 | 9/2006 | Carrison |
| 7,114,501 B2 | 10/2006 | Johnson et al. |
| 7,138,442 B2 | 11/2006 | Smith et al. |
| 7,153,306 B2 | 12/2006 | Ralph et al. |
| 7,153,307 B2 | 12/2006 | Scribner et al. |
| 7,156,843 B2 | 1/2007 | Skarda |

(56) References Cited

U.S. PATENT DOCUMENTS

| | | |
|---|---|---|
| 7,156,845 B2 | 1/2007 | Mulier |
| 7,166,121 B2 | 1/2007 | Reiley et al. |
| 7,172,629 B2 | 2/2007 | McKay et al. |
| 7,179,255 B2 | 2/2007 | Lettice et al. |
| 7,186,234 B2 | 3/2007 | Dahla et al. |
| 7,186,761 B2 | 3/2007 | Soffiati et al. |
| 7,226,481 B2 | 6/2007 | Kuslich et al. |
| 7,252,671 B2 | 8/2007 | Scribner et al. |
| 7,267,683 B2 | 9/2007 | Sharkey et al. |
| 7,270,661 B2 | 9/2007 | Dahla et al. |
| 7,294,127 B2 | 11/2007 | Leung |
| 7,465,318 B2 | 12/2008 | Sennett et al. |
| 7,480,533 B2 | 1/2009 | Cosman et al. |
| 7,503,920 B2 | 3/2009 | Siegal |
| 7,544,196 B2 | 6/2009 | Bagga et al. |
| 7,559,932 B2 | 7/2009 | Truckai et al. |
| 7,569,054 B2 | 8/2009 | Michelson |
| 7,572,263 B2 | 8/2009 | Preissman |
| 7,591,822 B2 | 9/2009 | Olson, Jr. et al. |
| 7,625,364 B2 | 12/2009 | Corcoran et al. |
| 7,641,664 B2 | 1/2010 | Pagano |
| 7,731,720 B2 | 6/2010 | Sand et al. |
| 7,811,291 B2 | 10/2010 | Liu et al. |
| 7,824,403 B2 | 11/2010 | Vaska |
| 7,842,041 B2 | 11/2010 | Liu et al. |
| 7,887,543 B2 | 2/2011 | Sand et al. |
| 7,905,884 B2 | 3/2011 | Simonton et al. |
| 7,918,874 B2 | 4/2011 | Siegal |
| 7,972,340 B2 | 7/2011 | Sand et al. |
| 7,976,542 B1 | 7/2011 | Cosman |
| 8,034,071 B2 | 10/2011 | Scribner et al. |
| 8,246,627 B2 | 8/2012 | Vanleeuwen et al. |
| 8,518,036 B2 | 8/2013 | Leung |
| 8,583,260 B2 | 11/2013 | Knudson |
| 8,591,507 B2 | 11/2013 | Kramer et al. |
| 8,663,226 B2 | 3/2014 | Germain |
| RE44,883 E | 5/2014 | Cha |
| 8,758,349 B2 | 6/2014 | Germain et al. |
| 8,827,981 B2 | 9/2014 | Liu et al. |
| 8,864,760 B2 | 10/2014 | Kramer et al. |
| 8,936,631 B2 | 1/2015 | Nguyen |
| 9,113,974 B2 | 8/2015 | Germain |
| 9,125,671 B2 | 9/2015 | Germain et al. |
| 9,161,809 B2 | 10/2015 | Germain et al. |
| 9,421,057 B2 | 8/2016 | Germain |
| 9,743,938 B2 | 8/2017 | Germain et al. |
| 2001/0011174 A1 | 8/2001 | Reiley et al. |
| 2001/0023349 A1 | 9/2001 | Van Tassel et al. |
| 2002/0007180 A1 | 1/2002 | Wittenberger et al. |
| 2002/0013600 A1 | 1/2002 | Scribner et al. |
| 2002/0026195 A1 | 2/2002 | Layne et al. |
| 2002/0026197 A1 | 2/2002 | Foley et al. |
| 2002/0068929 A1 | 6/2002 | Zvuloni |
| 2002/0068974 A1 | 6/2002 | Kuslich et al. |
| 2002/0077595 A1 | 6/2002 | Hundertmark et al. |
| 2002/0082605 A1 | 6/2002 | Reiley et al. |
| 2002/0115742 A1 | 8/2002 | Trieu et al. |
| 2002/0128638 A1 | 9/2002 | Chauvel et al. |
| 2002/0133148 A1 | 9/2002 | Daniel et al. |
| 2002/0156483 A1 | 10/2002 | Voellmicke et al. |
| 2002/0188299 A1 | 12/2002 | Reiley et al. |
| 2002/0188300 A1 | 12/2002 | Arramon et al. |
| 2003/0014094 A1 | 1/2003 | Hammack et al. |
| 2003/0032929 A1 | 2/2003 | McGuckin |
| 2003/0036763 A1 | 2/2003 | Bhatnagar et al. |
| 2003/0043963 A1 | 3/2003 | Yamagami et al. |
| 2003/0050644 A1 | 3/2003 | Boucher et al. |
| 2003/0069522 A1 | 4/2003 | Jasobsen et al. |
| 2003/0073979 A1 | 4/2003 | Naimark et al. |
| 2003/0130664 A1 | 7/2003 | Boucher et al. |
| 2003/0163085 A1 | 8/2003 | Tanner et al. |
| 2003/0191489 A1 | 10/2003 | Reiley et al. |
| 2003/0195547 A1 | 10/2003 | Scribner et al. |
| 2003/0212394 A1 | 11/2003 | Pearson et al. |
| 2003/0212395 A1 | 11/2003 | Woloszko et al. |
| 2003/0220414 A1 | 11/2003 | Axen et al. |
| 2003/0225432 A1 | 12/2003 | Baptiste et al. |
| 2003/0233096 A1 | 12/2003 | Osorio et al. |
| 2004/0023384 A1 | 2/2004 | Fukaya |
| 2004/0023784 A1 | 2/2004 | Yu et al. |
| 2004/0024081 A1 | 2/2004 | Trieu et al. |
| 2004/0024398 A1 | 2/2004 | Hovda et al. |
| 2004/0024409 A1 | 2/2004 | Sand et al. |
| 2004/0024410 A1 | 2/2004 | Olson et al. |
| 2004/0034384 A1 | 2/2004 | Fukaya |
| 2004/0044096 A1 | 3/2004 | Smith et al. |
| 2004/0044350 A1 | 3/2004 | Martin et al. |
| 2004/0059328 A1 | 3/2004 | Daniel et al. |
| 2004/0087936 A1 | 5/2004 | Stern et al. |
| 2004/0087994 A1 | 5/2004 | Suddaby |
| 2004/0092946 A1 | 5/2004 | Bagga et al. |
| 2004/0097612 A1 | 5/2004 | Rosenberg et al. |
| 2004/0111136 A1 | 6/2004 | Sharkey et al. |
| 2004/0127987 A1 | 7/2004 | Evans et al. |
| 2004/0133208 A1 | 7/2004 | Weikel et al. |
| 2004/0138758 A1 | 7/2004 | Evans et al. |
| 2004/0153064 A1 | 8/2004 | Foley et al. |
| 2004/0153115 A1 | 8/2004 | Reiley et al. |
| 2004/0158237 A1 | 8/2004 | Abboud et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0210231 A1 | 10/2004 | Broucher et al. |
| 2004/0215343 A1 | 10/2004 | Hochschuler et al. |
| 2004/0220577 A1 | 11/2004 | Cragg |
| 2004/0220680 A1 | 11/2004 | Yamamoto et al. |
| 2004/0225296 A1 | 11/2004 | Reiss et al. |
| 2004/0226479 A1 | 11/2004 | Lyles et al. |
| 2004/0230309 A1 | 11/2004 | Dimauro et al. |
| 2004/0236186 A1 | 11/2004 | Chu |
| 2004/0247644 A1 | 12/2004 | Bratt et al. |
| 2004/0267271 A9 | 12/2004 | Scribner et al. |
| 2005/0027245 A1 | 2/2005 | Sachdeva et al. |
| 2005/0033303 A1 | 2/2005 | Chappuis et al. |
| 2005/0038383 A1 | 2/2005 | Kelley et al. |
| 2005/0038422 A1 | 2/2005 | Maurice |
| 2005/0043737 A1 | 2/2005 | Reiley et al. |
| 2005/0055030 A1 | 3/2005 | Falahee |
| 2005/0060030 A1 | 3/2005 | Lashinski et al. |
| 2005/0070844 A1 | 3/2005 | Chow et al. |
| 2005/0070912 A1 | 3/2005 | Voellmicke |
| 2005/0070915 A1 | 3/2005 | Mazzuca et al. |
| 2005/0090852 A1 | 4/2005 | Layne et al. |
| 2005/0113836 A1 | 5/2005 | Lozier et al. |
| 2005/0119650 A1 | 6/2005 | Sanders et al. |
| 2005/0124989 A1 | 6/2005 | Suddaby |
| 2005/0143827 A1 | 6/2005 | Globerman et al. |
| 2005/0177168 A1 | 8/2005 | Brunnett et al. |
| 2005/0177210 A1 | 8/2005 | Lueng et al. |
| 2005/0182412 A1 | 8/2005 | Johnson et al. |
| 2005/0182413 A1 | 8/2005 | Johnson et al. |
| 2005/0187556 A1 | 8/2005 | Stack et al. |
| 2005/0199156 A1 | 9/2005 | Khairoun et al. |
| 2005/0209557 A1 | 9/2005 | Carroll et al. |
| 2005/0216018 A1 | 9/2005 | Sennett |
| 2005/0228391 A1 | 10/2005 | Levy et al. |
| 2005/0234425 A1 | 10/2005 | Miller et al. |
| 2005/0240193 A1 | 10/2005 | Layne et al. |
| 2005/0251266 A1 | 11/2005 | Maspero et al. |
| 2005/0251267 A1 | 11/2005 | Winterbottom et al. |
| 2005/0261683 A1 | 11/2005 | Veldhuizen et al. |
| 2005/0283148 A1 | 12/2005 | Janssen |
| 2005/0287771 A1 | 12/2005 | Seamons et al. |
| 2006/0024348 A1 | 2/2006 | Engqvist et al. |
| 2006/0025763 A1 | 2/2006 | Nelson et al. |
| 2006/0041033 A1 | 2/2006 | Bisig et al. |
| 2006/0052743 A1 | 3/2006 | Reynolds |
| 2006/0064101 A1 | 3/2006 | Arramon |
| 2006/0074433 A1 | 4/2006 | McGill et al. |
| 2006/0084977 A1 | 4/2006 | Lieberman |
| 2006/0085009 A1 | 4/2006 | Truckai et al. |
| 2006/0100635 A1 | 5/2006 | Reiley et al. |
| 2006/0100706 A1 | 5/2006 | Shadduck et al. |
| 2006/0106392 A1 | 5/2006 | Embry |

(56) References Cited

U.S. PATENT DOCUMENTS

| | | |
|---|---|---|
| 2006/0106459 A1 | 5/2006 | Truckai et al. |
| 2006/0116689 A1 | 6/2006 | Albans et al. |
| 2006/0116690 A1 | 6/2006 | Pagano |
| 2006/0122623 A1 | 6/2006 | Truckai et al. |
| 2006/0142732 A1 | 6/2006 | Karmarkar et al. |
| 2006/0149268 A1 | 7/2006 | Truckai et al. |
| 2006/0149281 A1 | 7/2006 | Reiley et al. |
| 2006/0156959 A1 | 7/2006 | Engqvist et al. |
| 2006/0184106 A1 | 8/2006 | McDaniel et al. |
| 2006/0184192 A1 | 8/2006 | Markworth et al. |
| 2006/0200121 A1 | 9/2006 | Mowery |
| 2006/0206116 A1 | 9/2006 | Yeung |
| 2006/0206136 A1 | 9/2006 | Sachdeva et al. |
| 2006/0217704 A1 | 9/2006 | Cockburn et al. |
| 2006/0217736 A1 | 9/2006 | Kaneko |
| 2006/0229625 A1 | 10/2006 | Truckai et al. |
| 2006/0229631 A1 | 10/2006 | Reiley et al. |
| 2006/0235417 A1 | 10/2006 | Sala |
| 2006/0259023 A1 | 11/2006 | Abboud et al. |
| 2006/0264819 A1 | 11/2006 | Fischer et al. |
| 2006/0264945 A1 | 11/2006 | Edidin et al. |
| 2006/0266372 A1 | 11/2006 | Miller et al. |
| 2006/0270750 A1 | 11/2006 | Almen et al. |
| 2006/0271061 A1 | 11/2006 | Beyar et al. |
| 2006/0276797 A1 | 12/2006 | Botimer |
| 2006/0276819 A1 | 12/2006 | Osorio et al. |
| 2006/0293687 A1 | 12/2006 | Bogert |
| 2007/0006692 A1 | 1/2007 | Phan |
| 2007/0010845 A1 | 1/2007 | Gong et al. |
| 2007/0016130 A1 | 1/2007 | Leeflang et al. |
| 2007/0016211 A1 | 1/2007 | Botimer |
| 2007/0021769 A1 | 1/2007 | Scribner et al. |
| 2007/0043373 A1 | 2/2007 | Sala |
| 2007/0055201 A1 | 3/2007 | Seto et al. |
| 2007/0055260 A1 | 3/2007 | Cragg |
| 2007/0055266 A1 | 3/2007 | Osorio et al. |
| 2007/0055275 A1 | 3/2007 | Schaller |
| 2007/0055277 A1 | 3/2007 | Osorio et al. |
| 2007/0055278 A1 | 3/2007 | Osorio et al. |
| 2007/0055279 A1 | 3/2007 | Sand et al. |
| 2007/0055281 A1 | 3/2007 | Osorio et al. |
| 2007/0055283 A1 | 3/2007 | Scribner |
| 2007/0055284 A1 | 3/2007 | Osorio |
| 2007/0055285 A1 | 3/2007 | Osorio et al. |
| 2007/0055300 A1 | 3/2007 | Osorio et al. |
| 2007/0055382 A1 | 3/2007 | Osorio et al. |
| 2007/0059281 A1 | 3/2007 | Moseley et al. |
| 2007/0067034 A1 | 3/2007 | Chirico et al. |
| 2007/0093840 A1 | 4/2007 | Pacelli |
| 2007/0114248 A1 | 5/2007 | Kovac |
| 2007/0118142 A1 | 5/2007 | Krueger et al. |
| 2007/0118143 A1 | 5/2007 | Ralph et al. |
| 2007/0142842 A1 | 6/2007 | Krueger et al. |
| 2007/0156130 A1 | 7/2007 | Thistle |
| 2007/0162042 A1 | 7/2007 | Dunker |
| 2007/0173939 A1 | 7/2007 | Kim et al. |
| 2007/0185231 A1 | 8/2007 | Liu et al. |
| 2007/0197935 A1 | 8/2007 | Reiley |
| 2007/0198023 A1 | 8/2007 | Sand et al. |
| 2007/0203500 A1 | 8/2007 | Gordon |
| 2007/0211563 A1 | 9/2007 | Devries |
| 2007/0233146 A1 | 10/2007 | Henniges et al. |
| 2007/0260223 A1 | 11/2007 | Scheibe et al. |
| 2007/0260257 A1 | 11/2007 | Phan |
| 2007/0270876 A1 | 11/2007 | Kuo et al. |
| 2007/0276319 A1 | 11/2007 | Betts |
| 2007/0282305 A1 | 12/2007 | Goldfarb et al. |
| 2008/0004615 A1 | 1/2008 | Woloszko et al. |
| 2008/0033422 A1 | 2/2008 | Turner et al. |
| 2008/0058725 A1 | 3/2008 | Scribner et al. |
| 2008/0058821 A1 | 3/2008 | Maurer et al. |
| 2008/0058827 A1 | 3/2008 | Osorio et al. |
| 2008/0058840 A1 | 3/2008 | Albrecht |
| 2008/0065020 A1 | 3/2008 | Ralph et al. |
| 2008/0065087 A1 | 3/2008 | Osorio et al. |
| 2008/0065137 A1* | 3/2008 | Boucher ............... A61B 17/68 606/191 |
| 2008/0065190 A1 | 3/2008 | Osorio et al. |
| 2008/0086142 A1 | 4/2008 | Kohm et al. |
| 2008/0140079 A1 | 6/2008 | Osorio et al. |
| 2008/0183165 A1 | 7/2008 | Buysee et al. |
| 2008/0183265 A1 | 7/2008 | Bly |
| 2008/0195112 A1 | 8/2008 | Liu et al. |
| 2008/0208255 A1 | 8/2008 | Siegal |
| 2008/0221608 A1 | 9/2008 | Betts |
| 2008/0228192 A1 | 9/2008 | Beyer et al. |
| 2008/0249481 A1 | 10/2008 | Crainich |
| 2008/0249525 A1 | 10/2008 | Lee et al. |
| 2008/0255571 A1 | 10/2008 | Truckai et al. |
| 2008/0269766 A1 | 10/2008 | Justis |
| 2008/0269796 A1 | 10/2008 | Reiley et al. |
| 2008/0287741 A1 | 11/2008 | Ostrovsky et al. |
| 2008/0294167 A1 | 11/2008 | Schumacher et al. |
| 2009/0076517 A1 | 3/2009 | Reiley et al. |
| 2009/0105775 A1 | 4/2009 | Mitchell et al. |
| 2009/0131867 A1 | 5/2009 | Liu et al. |
| 2009/0131886 A1 | 5/2009 | Liu et al. |
| 2009/0131945 A1 | 5/2009 | Liu et al. |
| 2009/0131948 A1 | 5/2009 | Liu |
| 2009/0131950 A1 | 5/2009 | Liu et al. |
| 2009/0131986 A1 | 5/2009 | Lee |
| 2009/0182427 A1 | 7/2009 | Liu et al. |
| 2009/0198243 A1 | 8/2009 | Melsheimer |
| 2009/0264862 A1 | 10/2009 | Neidert et al. |
| 2009/0264892 A1 | 10/2009 | Beyar et al. |
| 2009/0292289 A9 | 11/2009 | Sand et al. |
| 2009/0293687 A1 | 12/2009 | Nino et al. |
| 2009/0299282 A1 | 12/2009 | Lau et al. |
| 2010/0057087 A1 | 3/2010 | Cha |
| 2010/0082033 A1 | 4/2010 | Germain |
| 2010/0114184 A1 | 5/2010 | Degtyar |
| 2010/0121332 A1 | 5/2010 | Crainich et al. |
| 2010/0152724 A1 | 6/2010 | Marion et al. |
| 2010/0160922 A1 | 6/2010 | Liu et al. |
| 2010/0211076 A1 | 8/2010 | Germain et al. |
| 2010/0274270 A1 | 10/2010 | Patel |
| 2010/0298832 A1* | 11/2010 | Lau ............... A61B 17/8819 606/86 R |
| 2011/0034884 A9 | 2/2011 | Pellegrino et al. |
| 2011/0098701 A1 | 4/2011 | McIntyre et al. |
| 2011/0160737 A1 | 6/2011 | Steffen et al. |
| 2011/0190831 A1 | 8/2011 | Mafi et al. |
| 2011/0251615 A1 | 10/2011 | Truckai et al. |
| 2011/0295261 A1 | 12/2011 | Germain |
| 2011/0295262 A1 | 12/2011 | Germain et al. |
| 2011/0301590 A1 | 12/2011 | Podhajsky et al. |
| 2012/0065543 A1 | 3/2012 | Ireland |
| 2012/0130381 A1 | 5/2012 | Germain |
| 2012/0143298 A1 | 6/2012 | Just et al. |
| 2012/0158004 A1 | 6/2012 | Burger et al. |
| 2012/0191095 A1 | 7/2012 | Burger et al. |
| 2012/0239049 A1 | 9/2012 | Truckai |
| 2012/0265186 A1 | 10/2012 | Burger et al. |
| 2012/0277582 A1 | 11/2012 | Mafi |
| 2012/0277730 A1 | 11/2012 | Salahieh |
| 2012/0330180 A1 | 12/2012 | Pellegrino et al. |
| 2012/0330301 A1 | 12/2012 | Pellegrino et al. |
| 2013/0006232 A1* | 1/2013 | Pellegrino ............... A61N 5/00 606/33 |
| 2013/0006257 A1 | 1/2013 | Lee |
| 2013/0041377 A1 | 2/2013 | Kuntz |
| 2013/0072941 A1 | 3/2013 | Tan-Malecki et al. |
| 2013/0197563 A1 | 8/2013 | Saab et al. |
| 2013/0231654 A1 | 9/2013 | Germain |
| 2013/0237795 A1 | 9/2013 | Carr |
| 2013/0261615 A1 | 10/2013 | Kramer et al. |
| 2013/0261621 A1 | 10/2013 | Kramer et al. |
| 2013/0345709 A1 | 12/2013 | Burger et al. |
| 2014/0135779 A1 | 5/2014 | Germain |
| 2014/0163566 A1 | 6/2014 | Phan et al. |
| 2014/0236144 A1 | 8/2014 | Krueger et al. |
| 2014/0316413 A1 | 10/2014 | Burger et al. |
| 2014/0350542 A1 | 11/2014 | Kramer et al. |

(56) References Cited

U.S. PATENT DOCUMENTS

| | | | |
|---|---|---|---|
| 2014/0357983 A1* | 12/2014 | Toomey | A61B 8/481 600/424 |
| 2014/0371740 A1 | 12/2014 | Germain et al. | |
| 2015/0216594 A1 | 8/2015 | Prakash | |
| 2015/0297246 A1 | 10/2015 | Patel et al. | |
| 2015/0313614 A1 | 11/2015 | Germain | |
| 2016/0120584 A1 | 5/2016 | Tieu et al. | |
| 2016/0228131 A1 | 8/2016 | Brockman et al. | |
| 2017/0095291 A1 | 4/2017 | Harrington | |
| 2018/0264231 A1* | 9/2018 | Scheibe | A61M 25/0133 |
| 2020/0078066 A1 | 3/2020 | Purdy et al. | |

FOREIGN PATENT DOCUMENTS

| | | |
|---|---|---|
| CN | 2841051 | 11/2006 |
| DE | 20314010 | 1/2015 |
| EP | 3260069 A1 | 12/2017 |
| JP | 2004242936 | 9/2004 |
| JP | 2008510530 | 4/2008 |
| JP | 2008528081 | 7/2008 |
| JP | 2008541878 | 11/2008 |
| JP | 2010063887 | 3/2010 |
| JP | 2011500156 | 1/2011 |
| WO | 1993004634 | 3/1993 |
| WO | 1996013297 | 5/1996 |
| WO | 1996020752 | 7/1996 |
| WO | 1997003611 | 2/1997 |
| WO | 2002003870 | 1/2002 |
| WO | 2003101308 | 12/2003 |
| WO | 2005039390 | 5/2005 |
| WO | 2005122938 | 12/2005 |
| WO | 2006058223 A2 | 6/2006 |
| WO | 2007036815 | 4/2007 |
| WO | 2007087400 | 8/2007 |
| WO | 2008076330 | 6/2008 |
| WO | 2008084479 | 7/2008 |
| WO | 2009065085 A1 | 5/2009 |
| WO | 2009155319 | 12/2009 |
| WO | 2010039894 | 4/2010 |
| WO | 2010081187 | 7/2010 |
| WO | 2010135602 | 11/2010 |
| WO | 2010135606 | 11/2010 |
| WO | 2011066465 | 6/2011 |
| WO | 2011066465 A1 | 6/2011 |
| WO | 2011114602 | 9/2011 |
| WO | 2011137357 | 11/2011 |
| WO | 2011137377 | 11/2011 |
| WO | 2012071464 | 5/2012 |
| WO | 2013147990 | 10/2013 |
| WO | 2014093673 | 6/2014 |
| WO | 2016183178 | 11/2016 |

OTHER PUBLICATIONS

Office Action dated Jan. 26, 2011 for U.S. Appl. No. 11/941,764.
Office Action dated Jul. 12, 2010 for U.S. Appl. No. 11/941,764.
Office Action dated Jul. 12, 2017 for U.S. Appl. No. 13/083,411.
Office Action dated Jul. 25, 2011 for U.S. Appl. No. 11/941,733.
Office Action dated Jul. 29, 2013 for U.S. Appl. No. 13/098,116.
Office Action dated Jul. 30, 2013 for U.S. Appl. No. 13/083,411.
Office Action dated Sep. 1, 2010 for U.S. Appl. No. 12/029,428.
Office Action dated Sep. 6, 2017 for U.S. Appl. No. 15/211,359.
Office Action dated Sep. 26, 2017 for U.S. Appl. No. 15/388,598.
Office Action dated Oct. 2, 2018 for U.S. Appl. No. 14/139,372.
Office Action dated Nov. 7, 2019 for U.S. Appl. No. 15/675,315.
Office Action dated Dec. 3, 2012 for U.S. Appl. No. 12/571,174.
Office Action dated Dec. 9, 2009 for U.S. Appl. No. 12/262,064.
Office Action dated Jul. 12, 2016 for U.S. Appl. No. 14/887,007.
Office Action dated Sep. 10, 2013 for U.S. Appl. No. 12/571,174.
International Search Report and Written Opinion dated Jan. 22, 2009 for PCT/US2008/83698.
International Search Report and Written Opinion dated Feb. 7, 2018 for PCT/US2017/058303.
International Search Report and Written Opinion dated Feb. 21, 2018 for PCT/US2017/063281.
International Search Report and Written Opinion dated Mar. 30, 2018 for PCT/US2017/065328.
International Search Report and Written Opinion dated Apr. 23, 2016 for PCT/US2018/012372.
International Search Report and Written Opinion dated Jul. 20, 2010 for PCT/US2010/035687.
European Examination Report dated Jan. 27, 2022 for EP18180753.8.
International Search Report and Written Opinion dated Jul. 26, 2011 for PCT/US2011/034628.
International Search Report and Written Opinion dated Aug. 25, 2009 for PCT/US2009/035726.
International Search Report and Written Opinion dated Nov. 20, 2009 for PCT/US2009/059113.
Notice of Allowance dated Jan. 4, 2017 for U.S. Appl. No. 13/302,927.
Notice of Allowance dated Jan. 18, 2017 for U.S. Appl. No. 13/097,998.
Notice of Allowance dated Feb. 19, 2020 for U.S. Appl. No. 15/675,315.
Notice of Allowance dated Feb. 21, 2019 for U.S. Appl. No. 14/139,372.
Notice of Allowance dated Apr. 3, 2019 for U.S. Appl. No. 15/349,715.
Notice of Allowance dated Apr. 9, 2014 for U.S. Appl. No. 12/578,455.
Notice of Allowance dated Apr. 23, 2018 for U.S. Appl. No. 13/083,411.
Notice of Allowance dated May 3, 2017 for U.S. Appl. No. 14/815,620.
Notice of Allowance dated May 11, 2018 for U.S. Appl. No. 14/453,427.
Notice of Allowance dated May 26, 2015 for U.S. Appl. No. 13/098,116.
Notice of Allowance dated Aug. 8, 2019 for U.S. Appl. No. 15/836,125.
Notice of Allowance dated Aug. 9, 2019 for U.S. Appl. No. 15/836,241.
Notice of Allowance dated Aug. 24, 2018 for U.S. Appl. No. 15/388,598.
Notice of Allowance dated Sep. 20, 2019 for U.S. Appl. No. 15/793,509.
Notice of Allowance dated Oct. 28, 2016 for U.S. Appl. No. 13/853,397.
Notice of Allowance dated Nov. 8, 2013 for U.S. Appl. No. 12/578,455.
Notice of Allowance dated Nov. 9, 2017 for U.S. Appl. No. 14/815,812.
Notice of Allowance dated Nov. 18, 2016 for U.S. Appl. No. 13/097,998.
Notice of Allowance dated Nov. 25, 2013 for U.S. Appl. No. 12/571,174.
Notice of Allowance dated Nov. 25, 2016 for U.S. Appl. No. 13/853,397.
Notice of Allowance dated Dec. 13, 2018 for U.S. Appl. No. 15/917,454.
Notice of Allowance dated Dec. 28, 2017 for U.S. Appl. No. 15/211,359.
Notice of Allowance dated Aug. 31, 2016 for U.S. Appl. No. 14/887,007.
Office Action dated Jan. 18, 2017 for U.S. Appl. No. 14/815,620.
Office Action dated Jan. 26, 2017 for U.S. Appl. No. 14/815,812.
Office Action dated Feb. 3, 2016 for U.S. Appl. No. 13/853,397.
Office Action dated Feb. 10, 2015 for U.S. Appl. No. 13/083,411.
Office Action dated Feb. 23, 2010 for U.S. Appl. No. 11/941,733.
Office Action dated Feb. 23, 2010 for U.S. Appl. No. 11/941,764.
Office Action dated Mar. 1, 2017 for U.S. Appl. No. 15/211,359.
Office Action dated Jun. 11, 2020 for U.S. Appl. No. 15/822,864.
Office Action dated Jun. 12, 2009 for U.S. Appl. No. 11/941,733.
Office Action dated Jun. 21, 2013 for U.S. Appl. No. 13/215,098.
Office Action dated Jun. 22, 2018 for U.S. Appl. No. 15/917,454.
Office Action dated Jun. 25, 2015 for U.S. Appl. No. 13/853,397.
Office Action dated Jun. 29, 2018 for U.S. Appl. No. 15/449,591.
Office Action dated Jul. 11, 2017 for U.S. Appl. No. 14/815,812.

(56) References Cited

OTHER PUBLICATIONS

Office Action dated Oct. 30, 2018 for U.S. Appl. No. 15/349,715.
Office Action dated Nov. 3, 2008 for U.S. Appl. No. 11/941,764.
Office Action dated Nov. 3, 2008 for U.S. Appl. No. 12/029,428.
Office Action dated Nov. 5, 2008 for U.S. Appl. No. 11/941,733.
Office Action dated Nov. 12, 2013 for U.S. Appl. No. 13/083,411.
Office Action dated Nov. 25, 2016 for U.S. Appl. No. 13/083,411.
Office Action dated Dec. 2, 2009 for U.S. Appl. No. 12/029,428.
European Examination Report dated Dec. 19, 2017 for EP13767383.6.
European Search Report dated Jul. 1, 2019 for EP16793433.0.
European Search Report dated May 29, 2020 for EP17874650.9.
European Search Report dated Jun. 8, 2017 for EP17154660.9.
European Search Report dated Jun. 16, 2020 for EP17863626.2.
European Search Report dated Jul. 1, 2020 for EP17878602.6.
European Search Report dated Nov. 15, 2017 for EP09818476.5.
European Search Report dated Nov. 16, 2016 for EP14772615.2.
International Search Report and Written Opinion dated Jan. 9, 2012 for PCT/US2011/034185.
Office Action dated Mar. 21, 2011 for U.S. Appl. No. 12/029,428.
Office Action dated Apr. 19, 2018 for U.S. Appl. No. 15/388,598.
Office Action dated Apr. 24, 2017 for U.S. Appl. No. 14/453,427.
Office Action dated Apr. 26, 2010 for U.S. Appl. No. 12/029,428.
Office Action dated May 1, 2009 for U.S. Appl. No. 12/261,987.
Office Action dated May 5, 2010 for U.S. Appl. No. 11/941,764.
Office Action dated May 6, 2019 for U.S. Appl. No. 15/675,315.
Office Action dated May 13, 2009 for U.S. Appl. No. 12/029,428.
Office Action dated May 17, 2010 for U.S. Appl. No. 12/261,987.
Office Action dated May 21, 2014 for U.S. Appl. No. 13/098,116.
Office Action dated May 24, 2012 for U.S. Appl. No. 12/578,455.
Office Action dated May 31, 2016 for U.S. Appl. No. 14/815,620.
Office Action dated Jun. 4, 2018 for U.S. Appl. No. 15/349,715.
Office Action dated Jun. 8, 2009 for U.S. Appl. No. 11/941,764.
Office Action dated Jun. 10, 2020 for U.S. Appl. No. 15/822,944.
Office Action dated Dec. 11, 2009 for U.S. Appl. No. 12/261,987.
Office Action dated Dec. 20, 2019 for U.S. Appl. No. 15/862,441.
Office Action dated Dec. 26, 2019 for U.S. Appl. No. 15/822,864.
Office Action dated Feb. 27, 2013 for U.S. Appl. No. 12/578,455.
Disc-O-Tech confidence Cement System at http://www.disc-o-tech.com/Articles/Article.asp?CategoryID=4&ArticleID=168 accessed, ,Dec. 3, 2007.
Dai, et al., Bone-Particle-Impregnated Bone Cement: an in vivo weight-bearing study, Journal Biomedical Materials Search, vol. 25 ,Jul. 30, 1990 ,141-156.
Hasenwinkel, et al.,"A Novel High-Viscosity, Two-Solution Acrylic Bone Cement: Effect of Chemical Composition on Properties", J. Biomed Mater. Res. vol. 47, No. 1 ,1999 ,36-45.
Klawitter, et al.,Application of Porous Ceramics for the Attachment of Load Bearing Internal Orthopedic Applications, J. Biomed. Mater. Res. Symp., 2(1) ,1972 ,61-229.
Liu, et al.,Bone-Particle-Impregnanted Bone Cement: An In Vitro Study, Journal of Biomedical Materials Research, vol. 21 , 1987 ,247-261.
Park, et al.,Biomaterials: An Introduction—Second Edition, Plenum Press ,1992 ,177-178.
Park, et al.,The Materials Properties of Bone-Particle Impregnated PMMA, Journal of Biomedical Engineering, vol. 108 ,1986 ,141-148.
European Search Report dated Oct. 18, 2023 for EP20865049.9.

\* cited by examiner

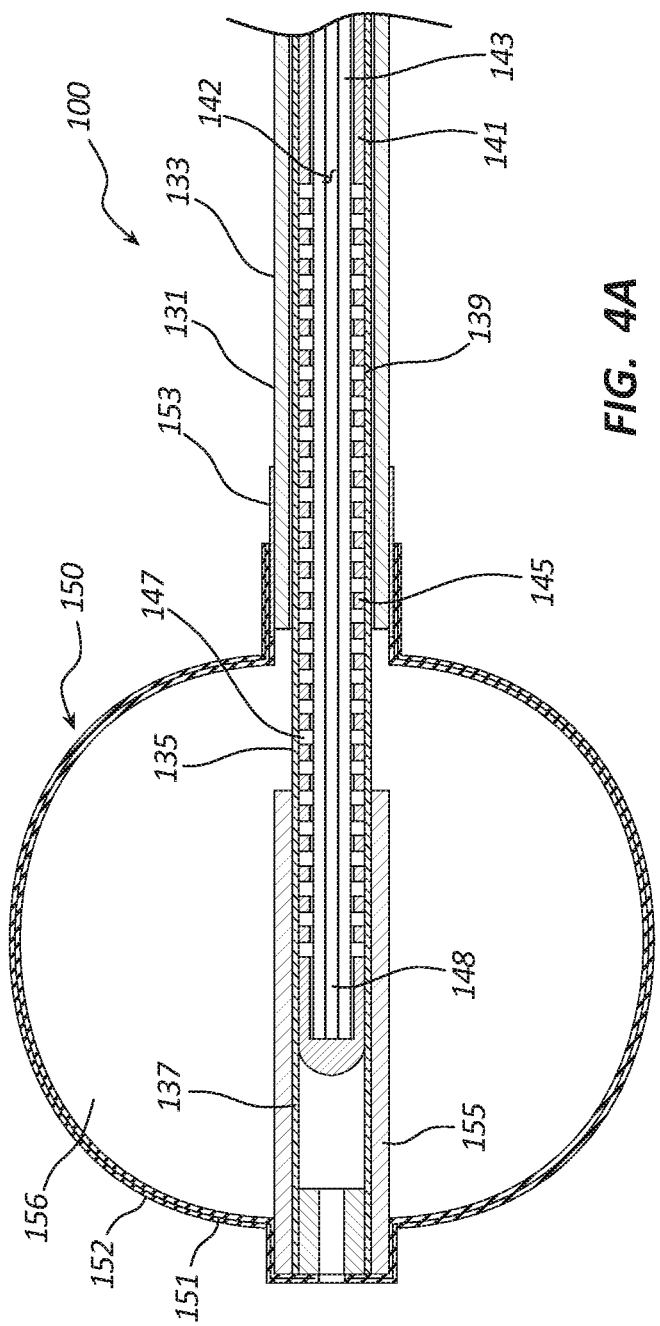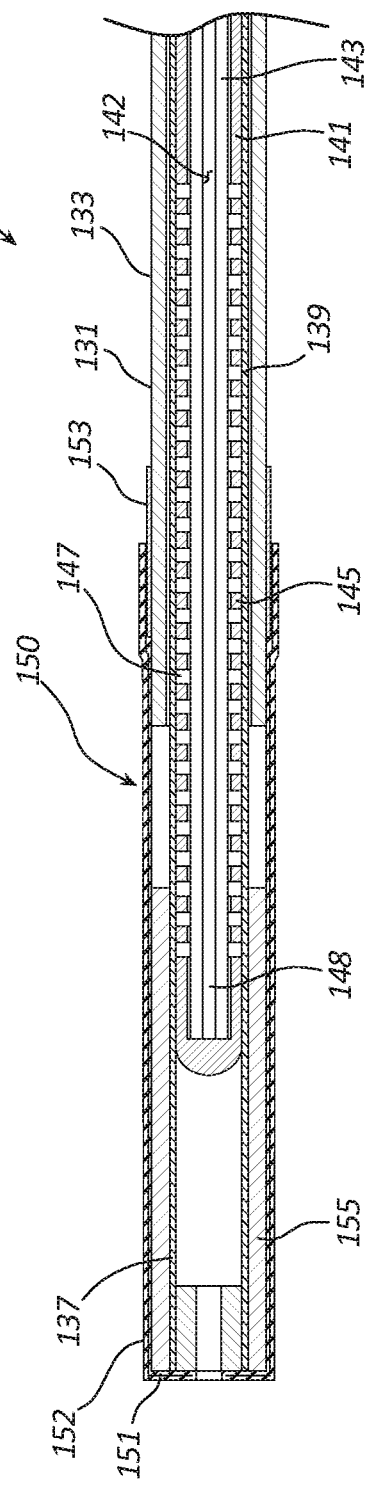
FIG. 4A
FIG. 4B

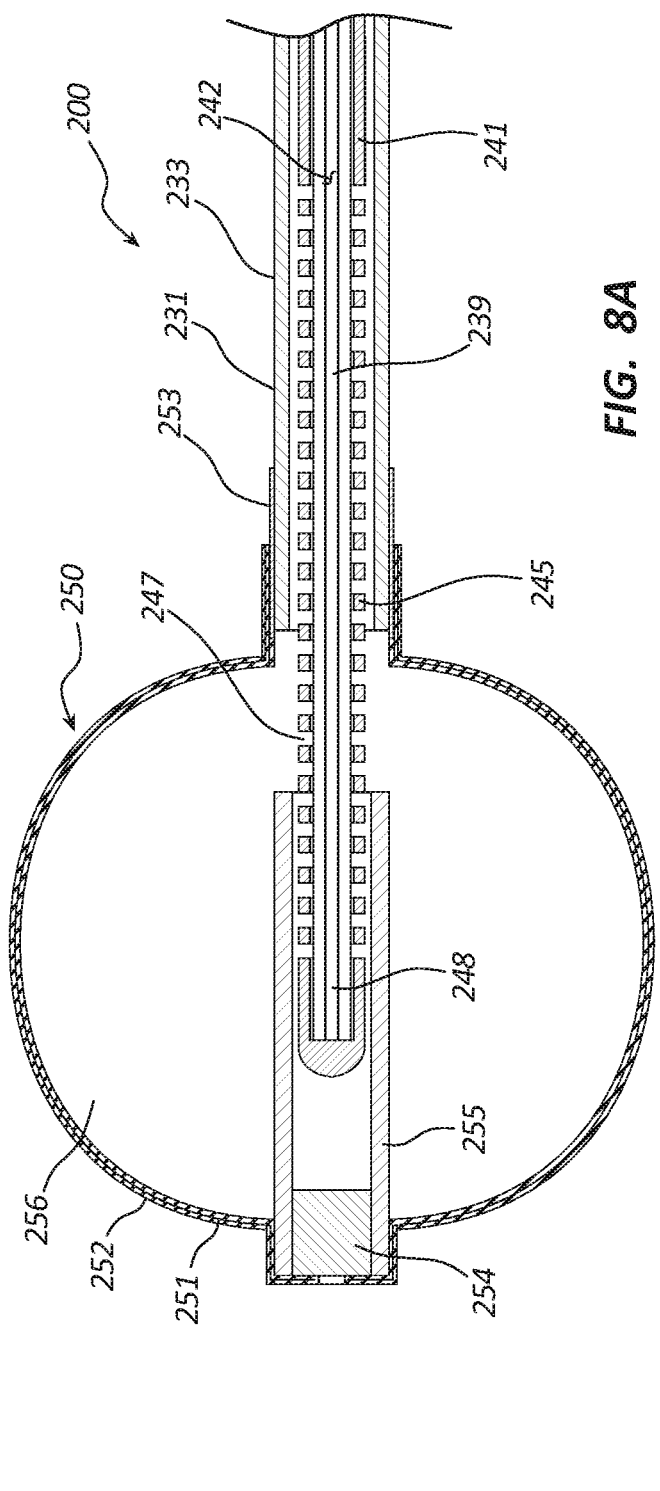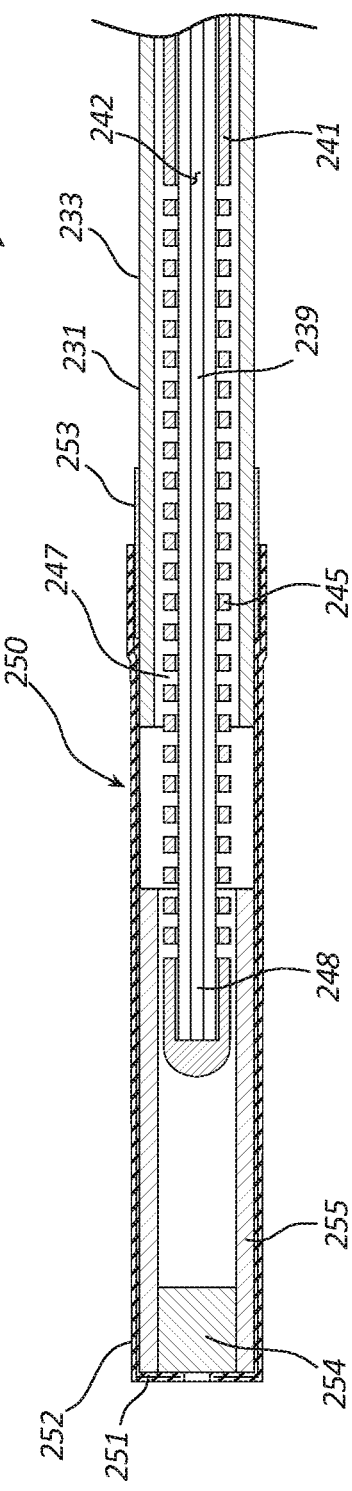
FIG. 8A
FIG. 8B

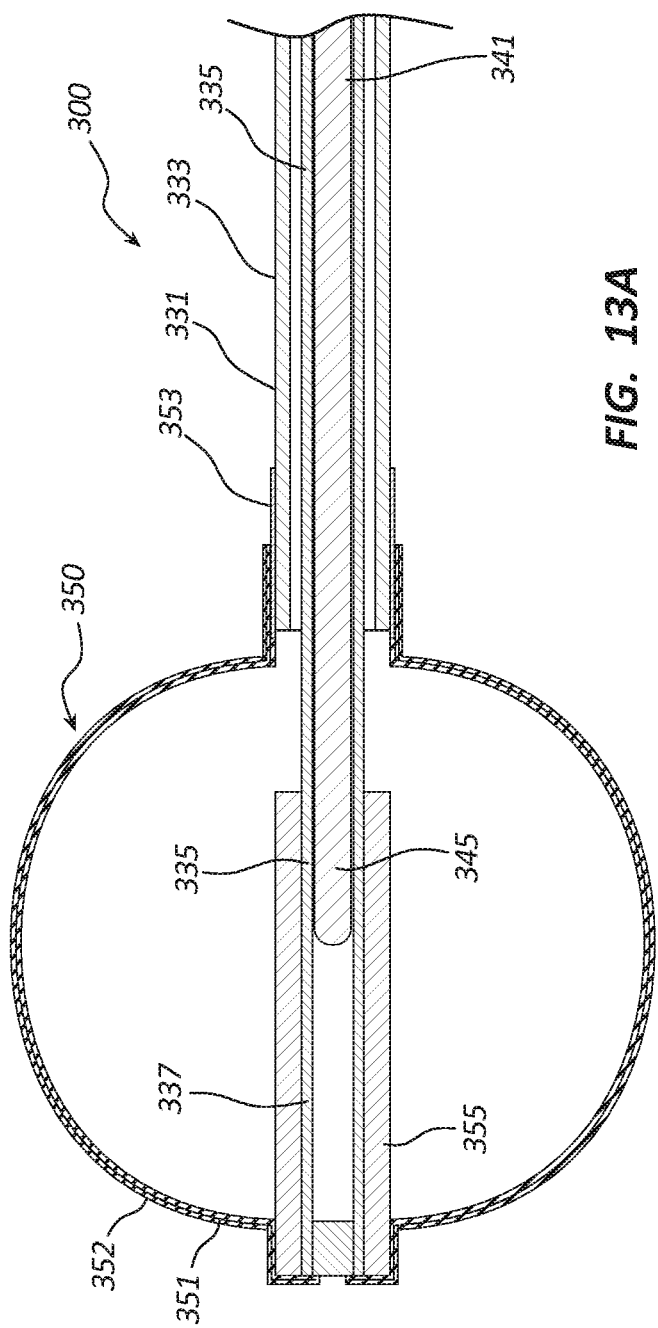
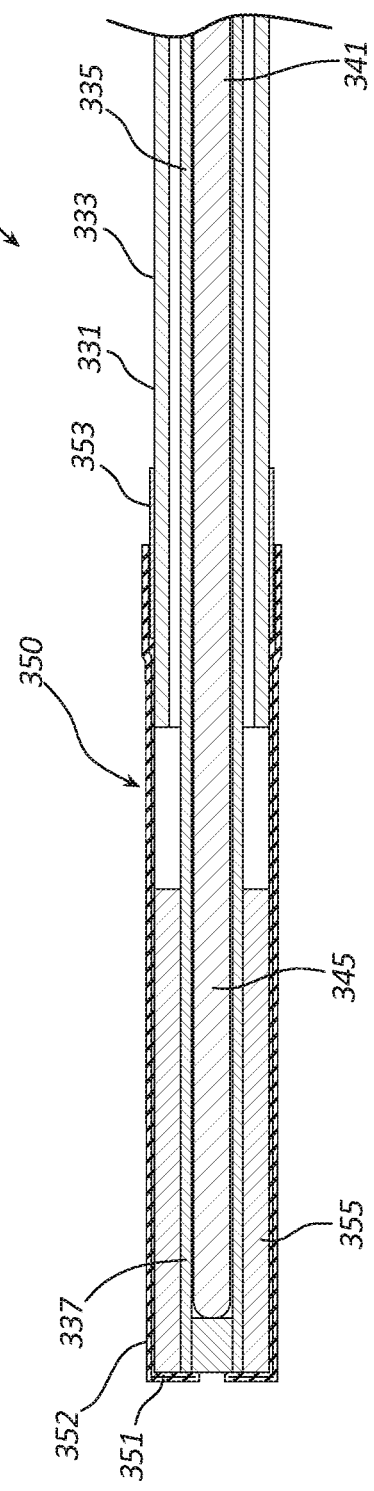

OSTEOTOME WITH INFLATABLE PORTION AND MULTIWIRE ARTICULATION

RELATED APPLICATIONS

This application claims priority to U.S. Provisional Patent Application No. 62/902,144, filed on Sep. 18, 2019 and titled, "Osteotome with Inflatable Portion and Multiwire Articulation," which is hereby incorporated by reference in its entirety.

TECHNICAL FIELD

The present disclosure relates generally to medical devices used to treat tissue, including bone. More specifically, in certain embodiments, the present disclosure relates to medical devices used to displace tissue using an expandable member, such as a balloon.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 4A is a longitudinal cross-sectional view of a distal portion of the bone displacement device of FIG. 1A in an "expandable member expanded" state.

FIG. 4B is a longitudinal cross-sectional view of the distal portion of the bone displacement device of FIG. 4A, in an "expandable member not expanded" state.

FIG. 8A is a longitudinal cross-sectional view of a distal portion of the bone displacement device of FIG. 5A in an "expandable member expanded" state.

FIG. 8B is a longitudinal cross-sectional view of the distal portion of the bone displacement device of FIG. 8A, in an "expandable member not expanded" state.

FIG. 13A is a longitudinal cross-sectional view of a distal portion of the bone displacement device of FIG. 9A in an "expandable member expanded" state.

FIG. 13B is a longitudinal cross-sectional view of the distal portion of the bone displacement device of FIG. 9A, in an "expandable member not expanded" state.

DETAILED DESCRIPTION

Figure 1A:
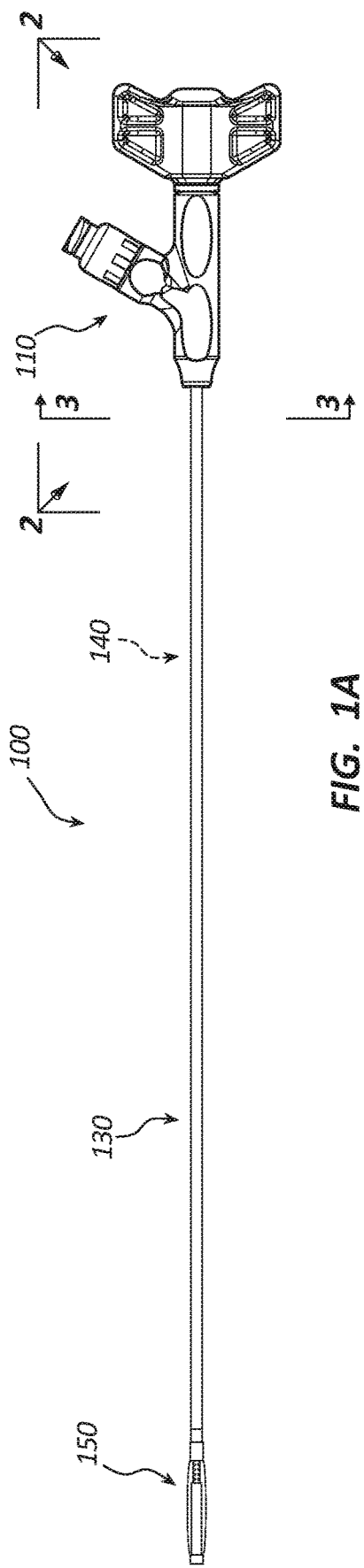
FIG. 1A is a side view of an embodiment of a bone displacement device in a ready state.

Tissue treatment devices may include elongate members, expandable members, and other components. In some instances, an elongate member of a tissue treatment device may be advanced to a treatment location and an expandable member expanded to displace tissue. For example, a bone displacement device may be disposed within a vertebra of a patient and an expandable member expanded to displace portions of the vertebra. Similarly, such devices may be utilized in other areas of the body with other types of tissue. For convenience, including when describing the illustrated embodiments, this disclosure references "bone displacement" or "bone displacement devices," however, such disclosure may be analogously applied to devices, elements, and procedures configured to displace or otherwise treat tissue in other portions of the body.

A bone displacement device may include an elongate outer tube. A stylet may be coaxially disposed within the outer tube. A proximal portion of the outer tube and the stylet shaft may be attached to a handle. In some embodiments, the stylet comprises a plurality of pull wires coaxially disposed within a shaft of the stylet. A distal portion of the stylet may be articulated when a tension force is applied to the plurality of pull wires. In some embodiments, a portion of the handle is configured as an actuator to articulate the stylet. For example, in some embodiments, the handle comprises a rotatable grip having female threads configured to engage with male threads of a pull member. The threads may include thread stops to limit rotation of the rotatable grip. A distal portion of the plurality of pull wires is coupled to the pull member. In such embodiments, rotation of the rotatable grip in the first direction proximally displaces the pull member and thus applies a tension force to the pull wires to articulate the distal portion of the stylet. The handle may also include a side port having a valve.

Certain bone displacement devices include an expandable member, such as a balloon. The expandable member may be disposed at a distal portion of the bone displacement device. In some embodiments, a proximal portion of the expandable member is attached to a distal portion of the outer tube via a tie layer. A distal portion of the expandable member can be attached to a tip tie tube. The tip tie tube may be longitudinally displaceable over the distal portion of the stylet. A protective sleeve may be disposed around the balloon when the bone displacement device is in its package, and displaced proximally over the outer tube to engage with the handle when the bone displacement device is ready to use.

In certain instances, a bone displacement device may be used by a practitioner to treat a fractured bone, such as a vertebral bone. The practitioner may displace bone by inflating an expandable member at a distal end of the bone displacement device to create a cavity into which a bone stabilizing material, such as bone cement, may be injected. The rotatable grip may be rotated in a first direction to apply a tension force to pull wires to articulate a distal portion of the bone displacement device. The distal portion of the bone displacement device may be directed—via articulation of the distal portion and/or displacement of the entire bone displacement device—to a desired location within the bone. The expandable member can be expanded to displace bone tissue adjacent the expandable member to create a cavity. The bone displacement device can be removed from the bone to allow for injection of bone cement into the cavity.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to a bone displacement device, the proximal end of the device refers to the end nearest the handle and the distal end refers to the opposite end, the end nearest a working tip of the device. If at one or more points in a procedure a physician changes the orientation of a bone displacement device, as used herein, the term "proximal end" always refers to the handle end of the device (even if the distal end is temporarily closer to the physician).

"Fluid" is used in its broadest sense, to refer to any fluid, including both liquids and gases as well as solutions, compounds, suspensions, etc., which generally behave as fluids.

FIGS. 1A-14B illustrate different views of several bone displacement devices or osteotomes and related components. In certain views each device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIGS. 1A-4B depict an embodiment of a bone displacement device 100. In the illustrated embodiment, the bone displacement device 100 comprises a handle 110, a catheter 130, a stylet 140, and an expandable member 150. FIG. 1A shows the bone displacement device 100 in a ready state where the expandable member 150 is not expanded and a distal portion of the bone displacement device 100 is not articulated. FIG. 1B shows the bone displacement device 100 in a bone displacement or cavity forming state where the expandable member 150 is expanded and the distal portion is articulated.

Figure 2:
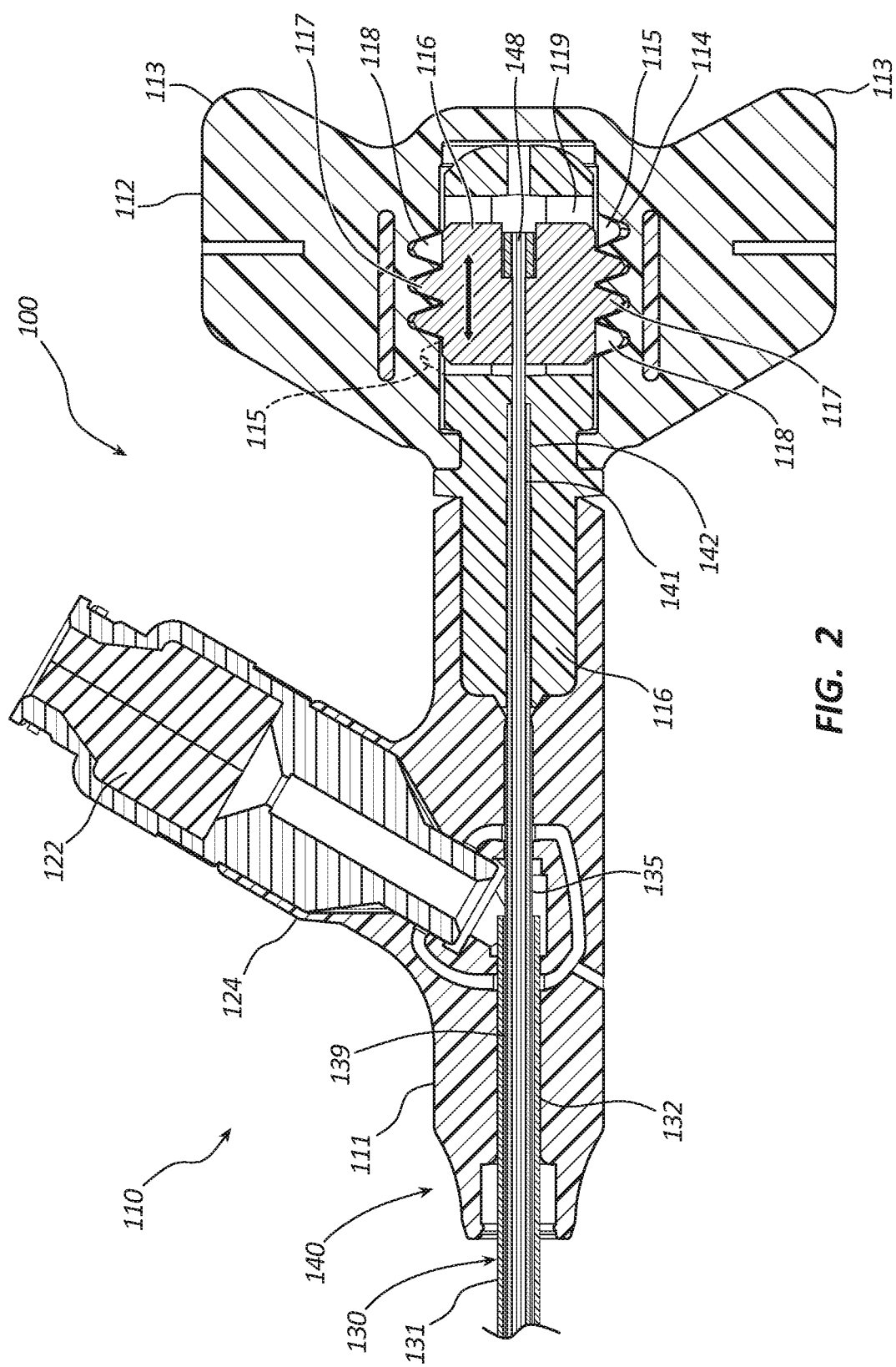
FIG. 2 is a longitudinal cross-sectional view of a proximal portion of the bone displacement device of FIG. 1A.

FIG. 2 illustrates a proximal portion of the bone displacement device 100. The proximal portion may comprise the handle 110, a proximal portion of the catheter 130, and a proximal portion of the stylet 140. The catheter 130 may comprise an elongate outer tube 131 and an elongate inner tube 135. The outer tube 131 may comprise a proximal portion 132. The outer tube 131 can be formed from any suitable polymeric material. For example, the outer tube 131 may be formed from polyurethane, nylon, PBT, polyethylene, polypropylene, etc. A proximal end of outer tube 131 can be fixedly coupled to the handle 110. In some embodiments, the inner tube 135 is coaxially disposed within the outer tube 131. The inner tube 135 may be formed from any of the materials listed in connection with the outer tube 131, though the inner tube 135 and outer tube 131 may or may not be formed of the same material. A proximal end of the inner tube 135 can be fixedly coupled to the handle 110 at a location proximal of the proximal end of the outer tube 131.

In the illustrated embodiment, the stylet 140 is shown to comprise a tubular shaft 141. The shaft 141 may be formed from any suitable rigid material, such as stainless steel, titanium, nitinol, etc. A proximal end of the shaft 141 may be fixedly coupled to the handle 110 at a location proximal of the proximal end of the inner tube 135. One or more pull wires 142 can be coaxially disposed within the shaft 141. In the illustrated embodiment, the pull wires 142 include a plurality of pull wires comprising seven pull wires. In other embodiments, the number of pull wires 142 may be three, four, five, six, eight, or more pull wires. The pull wires 142 may extend proximally from the shaft 141 and be fixedly coupled to the distal end of the shaft 141. The pull wires 142 may be formed from any suitable material with high tensile strength. For example, the pull wires 142 may be formed from stainless steel, titanium, nitinol, etc. A diameter of the pull wires 142 may range from about 0.005 inch to about 0.030 inch.

Figure 3:
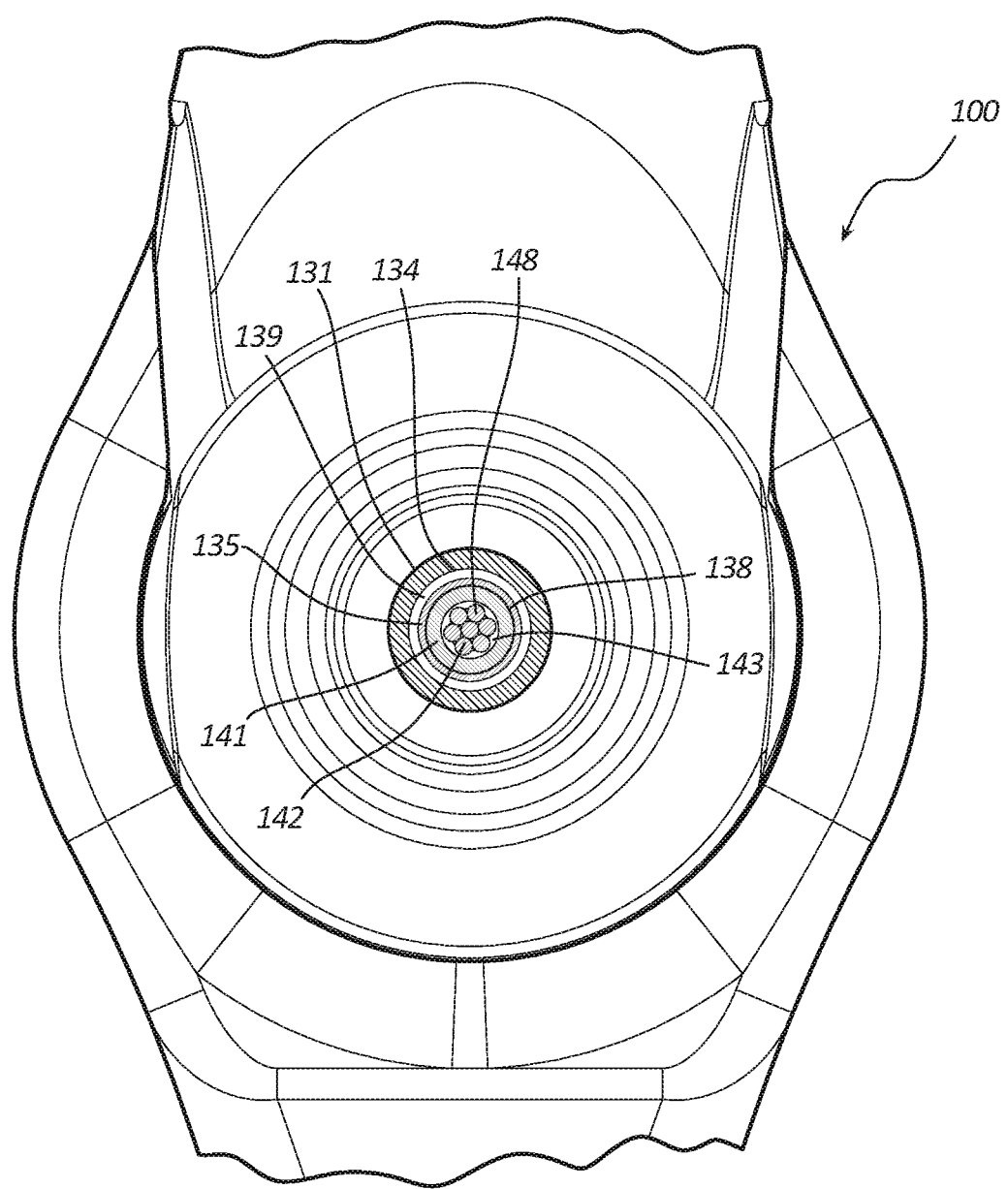
FIG. 3 is a transverse cross-sectional view of a middle portion of the bone displacement device of FIG. 1A.

FIG. 3 illustrates a transverse cross-section of a middle portion of the bone displacement device 100. As illustrated, the outer tube 131 includes an outer lumen 134. The inner tube 135 is shown to be coaxially disposed within the outer lumen 134. An annular space 139 may be formed between the outer tube 131 and the inner tube 135. The inner tube 135 may include an inner lumen 138. The shaft 141 may be coaxially disposed within the inner lumen 138. The shaft 141 is shown to include a shaft lumen 143. The pull wires 142 are disposed within the shaft lumen 143. As depicted in FIG. 3, the pull wires 142 collectively include seven individual pull wires 148. The individual pull wires 148 are disposed with a first individual pull wire 148 centrally located and the remaining six individual pull wires 148 equally spaced around the first individual pull wire 148. The pull wires 148 are shown as individual strands disposed longitudinally adjacent each other (without braiding or twisting) in the illustrated embodiment. This configuration of the pull wires 148 may be configured to provide adequate stiffness to the bone displacement device 100 to the ready state where the distal portion of the bone displacement device 100 is not articulated and/or to facilitate transfer of force to straighten the bone displacement device 100 from an articulated configuration to a non articulated configuration. In another embodiment, each pull wire 148 may be formed in a braid of a plurality of smaller diameter wires. Other arrangements of the pull wires 148 are likewise within the scope of this disclosure, including embodiments where the individual wires are braided or twisted into a cable.

Referring again to FIG. 2, the handle 110 may comprise a body 111 and a rotatable grip 112 rotatably coupled to a proximal end of the body 111. The body 111 and rotatable grip 112 may be formed from any suitable polymeric material, such as polycarbonate, acrylonitrile butadiene styrene, etc. The body 111 may comprise a side port 124. In the illustrated embodiment, the side port 124 extends generally proximally and laterally from a longitudinal axis of the body 111. The side port 124 may extend at an angle ranging from 15 degrees to 90 degrees or about 45 degrees relative to the longitudinal axis. The side port 124 may be in fluid communication with the annular space (139 of FIG. 3.) During some therapies, a fluid delivery device (e.g., syringe) can be releasably coupled to a proximal portion of the side port 124. A valve member 122 may be disposed within the side port 124. The valve member 122 may be configured to selectively permit air or fluid to be directed from the fluid delivery device, through the side port 124, through the annular space 139, and then to the expandable member (150 of FIG. 1A) when the fluid delivery device is coupled to the side port 124. The valve member 122 may also be configured to retain the air or fluid within the annular space 139 and the expandable member 150 when the fluid delivery device is removed from the side port 124.

In the illustrated embodiment, the proximal end of the outer tube 131 is coupled to the body 111 at a location distal to the side port 124, and the inner tube 135 is coupled to the body 111 at a location proximal to the side port 124. Further, a proximal end of the shaft 141 can be coupled to the body 111 at a location proximal to the inner tube 135.

The rotatable grip 112 may be configured to be rotated around a longitudinal axis of the handle 110. As depicted, the rotatable grip 112 may comprise laterally extending wings 113 configured to be gripped by a user. In other embodiments, the rotatable grip 112 may comprise any suitable feature to facilitate gripping and rotation of the rotatable grip 112. For example, the rotatable grip 112 may comprise a knob including grippable features, such as ridges, bumps, recesses, textured surface, etc.

The rotatable grip 112 may comprise a chamber 119 configured to receive a pull member 116. As shown in the figures, and discussed below, the pull member 116 of the illustrated embodiment is configured as non-rotatable relative to the rotatable grip 112, or configured not to rotate with the rotatable grip 112. The chamber 119 may include a female thread 114 configured to engage a male thread 117 of the pull member 116. The female thread 114 may comprise proximal and distal female thread stops 115. In the illustrated embodiment, the female thread stops 115 may include a flat face oriented perpendicular to a longitudinal axis of the rotatable grip 112. In another embodiment, the female thread stops 115 may include a tapered face. The pull member 116 may include a male thread 117 configured to engage with the female thread 114. The male thread 117 may comprise proximal and distal male thread stops 118. In the illustrated embodiment, the male thread stops 118 may include a flat face oriented perpendicular to a longitudinal axis of the pull member 116. In another embodiment, the male thread stops 118 may include a tapered face. The female thread stops 115 can be configured to engage with the male thread stops 118 to prevent over-rotation of the rotatable grip 112 in both a first direction and a second direction. In some instances, over-rotation of the rotatable grip 112 may result in excess strain or breakage of the shaft 141 and/or one or more of the individual pull wires 148. Thus, the threads may be configured with a positive stop to minimize excess force and subsequent breakage. In another embodiment, the chamber 119 may include a male thread 117 and male thread stops 118 while the pull member 116 includes a female thread 114 and female thread stops 115.

Figure 1B:
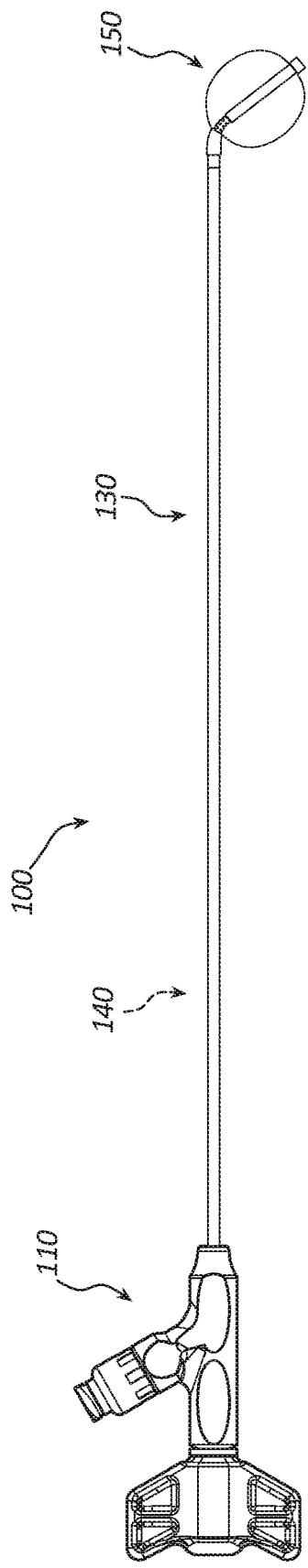
FIG. 1B is a side view of the bone displacement device of FIG. 1A in a bone displacement state.

In the illustrated embodiment, the proximal ends of the pull wires 142 may be fixedly coupled to the pull member 116. When the rotatable grip 112 is rotated in the first direction, the pull member 116 is displaced proximally, causing a tension force to be equally or substantially equally applied to all of the individual pull wires 148. Embodiments wherein one or more individual pull wires 148 transmit an uneven or larger portion of the tension force are likewise within the scope of this disclosure. The tension force on the pull wires 142 may result in a tension force being applied to the distal end of the stylet 140 and articulation of the distal portion of the bone displacement device 100, as shown in FIG. 1B. During actuation, the rotatable grip 112 may be rotated from about one degree to about 540 degrees, from about one degree to about 360 degrees, or from about one degree to about 180 degrees, or along any portion of these ranges. Rotation of the rotatable grip 112 in the first direction may be stopped when the proximal female thread stop 115 engages with the proximal male thread stop 118, or may be stopped at any point along the range of rotation of the rotatable grip 112, meaning it is stopped by a user at a point of partial rotation along the rotational range of the rotatable grip 112. Rotation of the rotatable grip 112 and proximal displacement of the pull member 116 may result in an articulation of the distal portion of the bone displacement device 100 from about zero degrees to about 180 degrees, from about zero degrees to about 135 degrees, or from about zero degrees to about 90 degrees. In some embodiments, the rotatable grip 112 may comprise a rotation lock configured to maintain the rotatable grip 112 in a partial or fully rotated state when the rotatable grip 112 is released by the user. For example, the body 111 may comprise teeth configured to engage with opposing teeth of the rotatable grip 112.

Rotation of the rotatable grip 112 in the second direction may displace the pull member 116 distally and release the tension force on the pull wires 142, resulting in the distal portion of the bone displacement device 100 returning to a straight configuration, as shown in FIG. 1A. The rotatable grip 112 can be rotated in the second direction until the distal female thread stop 115 engages with the distal male thread stop 118.

FIGS. 4A-4B illustrate a distal portion of the bone displacement device 100. The distal portion may comprise the expandable member 150, a distal portion 133 of the outer tube 131, a distal portion 137 of the inner tube 135, and a distal portion 145 of the shaft 141. The inner tube 135 and the shaft 141 may extend beyond a distal end of the outer tube 131. The inner tube 135 may extend beyond a distal end of the shaft 141. In the illustrated embodiment, the expandable member 150 comprises a balloon 151. In other embodiments, the expandable member 150 may comprise any suitable expandable and retractable mechanism. For example, the expandable member 150 may comprise a plurality of ribs configured to expand radially outward.

The balloon 151 may comprise a double balloon wall 152 configured to expand radially outward without stretching when air or fluid is injected into the balloon 151, for example, through the annular space 139. Embodiments wherein the balloon wall comprises more or fewer layers are likewise within the scope of this disclosure. A thickness of the double balloon wall 152 may range from about 0.020 mm to about 0.038 mm or from about 0.025 mm to about 0.030 mm. A length of the balloon 151 when not inflated or expanded may range from about 10 mm to about 30 mm. The balloon 151 may be formed of any suitable non-compliant polymeric material, such as engineered plastic polyurethane (e.g., Isoplast®), nylon, polybutylene terephthalate, etc. A proximal portion of the balloon 151 may be sealingly coupled to the distal end of the outer tube 131. A tie layer 153 may be disposed between the balloon wall 152 and the outer tube 131 to facilitate bonding of the balloon wall 152 to the outer tube 131. In other embodiments, the tie layer 153 is not used to facilitate bonding of the balloon wall 152 to the outer tube 131. The tie layer 153 may be formed from a polyurethane material having an intermediate hardness that is between the hardness of the material of the balloon 151 and the hardness of the material of the outer tube 131. The balloon wall 152 may be bonded to the tie layer 153 and the outer tube 131 using any suitable technique, such as heat, radio frequency, solvent bonding, gluing, etc.

A distal portion of the balloon 151 may be sealingly coupled to the distal end of the inner tube 135. A tip tie tube 155 may be disposed between the balloon wall 152 and the inner tube 135. The tip tie tube 155 may be formed from a material similar to the tie layer 153. In some embodiments, the tip tie tube 155 may comprise a braided structure. The tip tie tube 155 may extend proximally over the distal portion 137 of the inner tube 135 and the distal portion 145 of the shaft 141. The tip tie tube 155 and shaft 141 may configured in a "piston/cylinder" type arrangements where the shaft 141 is allowed to move with respect to the tip tie tube when the balloon 151 is inflated or deflated. For example, the tip tie tube 155 may be configured to piston proximally over the shaft 141 when the balloon 151 is inflated and to piston distally over the shaft 141 when the balloon 151 is deflated. The tip tie tube 155 may be configured to facilitate bonding of the balloon wall 152 to the inner tube 135. In other embodiments, the tip tie tube 155 may provide structural support to the inner tube 135 to prevent kinking of the inner tube 135 when inserted into a vertebral bone.

The seal of the proximal end of the balloon 151 to the outer tube 131 and the seal of the distal end of the balloon 151 to the inner tube 135 may form a balloon chamber 156 configured to be pressurized. The balloon chamber 156 may be pressurized up to a pressure of about 60 atm. The balloon 151 may be expanded to a diameter of from about 10 mm to about 30 mm.

As shown in FIGS. 4A-4B, the distal portion 145 of the shaft 141 may comprise a plurality of laser cuts 147. The laser cuts 147 may facilitate articulation of the shaft 141 in a single plane when the tension force is applied to the pull wires 142, as shown in FIG. 1B. The laser cuts 147 may comprise variables (e.g., depth, pitch, spacing) that control the articulation parameters of the shaft 141, such as angle of articulation. In certain embodiments, the laser cuts 147 may comprise a tab configured to be received by a recess. The laser cuts 147 of this embodiment may prevent torsional rotation of the laser cuts 147 relative to one another. The pull wires 142 may also prevent torsional rotation of the laser cuts 147 because the pull wires 142 substantially fill the shaft lumen 143 preventing axial misalignment of the laser cuts 147. The laser cuts 147 may extend partially through a diameter of the shaft 141, leaving a spine of uncut material. When articulated, the shaft 141 may bend toward the spine while a distance between shaft segments on either side of the laser cuts 147 increases on an opposing side of the shaft 141, defining a substantially "V" shape.

During use, in some instances, the shaft 141 may break at one of the laser cuts 147 when the shaft 141 is articulated. This may be due to external forces (such as from the bone) acting on the shaft 141. In the event of a breakage, the pull wires 142 may prevent a portion of the shaft 141 distal to the break from breaking away from a remainder of the shaft 141. Even if one of the individual pull wires 148 also breaks, the remaining individual pull wires 148 may retain attachment to the distal end of the shaft 141. Furthermore, embodiments wherein the pull wires 142 collectively fill the shaft lumen 143, even in an event of a break in the shaft 141, the pull wires 142 may maintain the coaxial arrangement of the shaft 141, inner tube 135, and outer tube 131 and prevent leakage of air or fluid from the bone displacement device 100 caused by damage to the inner tube 135 and/or outer tube 131 by a broken end of the shaft 141 of a pull wire 148.

In use, a bone displacement device may be used to displace bone tissue. A distal end of the bone displacement device may be inserted into a vertebral bone, for example, through an introducer cannula. A distal portion of the bone displacement device may be articulated when a rotatable grip is rotated in a first direction, causing one or more pull members to be displaced proximally. Proximal displacement of the pull member may apply a tension force to pull wires disposed within a stylet shaft and coupled to the pull member. The tension force applied to the pull wires can cause a distal portion of a stylet to articulate the distal portion of the bone displacement device. The articulated bone displacement device can be directed to a desired location within the vertebral bone. A syringe may be coupled to a side port of a handle. Air or fluid may be delivered through the side port to an expandable member (e.g., balloon) disposed adjacent the distal end of the bone displacement device. The air or fluid may expand the expandable member to displace adjacent bone tissue.

FIGS. 5A-8B depict an embodiment of a bone displacement device 200 that resembles the bone displacement device 100 described above in certain respects. Accordingly, like features are designated with like reference numerals, with the leading digit incremented to "2." For example, the embodiment depicted in FIGS. 5A-8B includes a handle 210 that may, in some respects, resemble the handle 110 of FIG. 1A. Relevant disclosure set forth above regarding similarly identified features thus may not be repeated hereafter. Moreover, specific features of the bone displacement device 100 and related components shown in FIGS. 1A-4A may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the bone displacement device 200 and related components depicted in FIGS. 5A-8B. Any suitable combination of the features, and variations of the same, described with respect to the bone displacement device 100 and related components illustrated in FIGS. 1A-4B can be employed with the bone displacement device 200 and related components of FIGS. 5A-8B, and vice versa. This pattern of disclosure applies equally to further embodiments depicted in subsequent figures and described hereafter, wherein the leading digits may be further incremented.

Figure 5A:
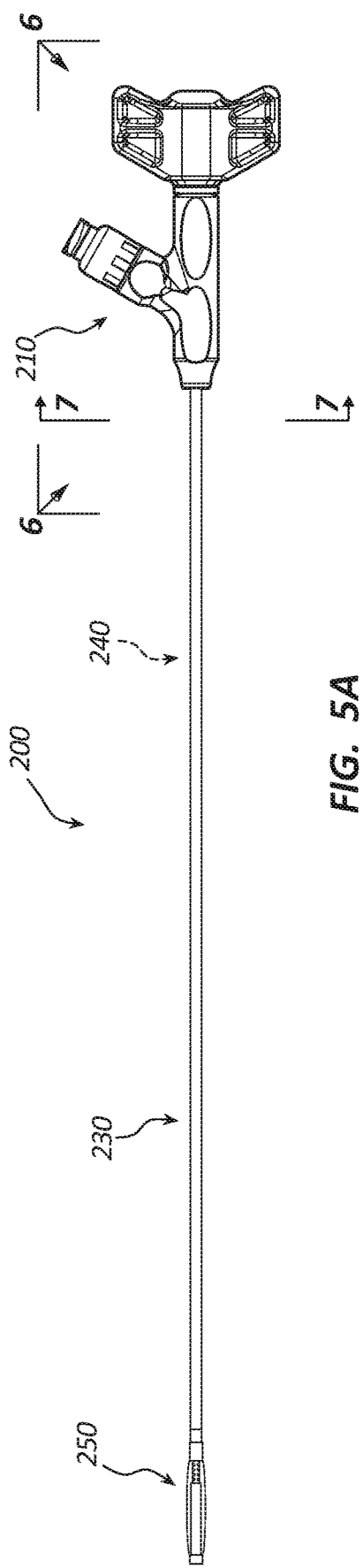
FIG. 5A is a side view of another embodiment of a bone displacement device in a ready state.

FIGS. 5A-8B depict another embodiment of a bone displacement device 200. In the illustrated embodiment of FIGS. 5A-8B, the bone displacement device 200 comprises a handle 210, a catheter 230, a stylet 240, and an expandable member 250. FIG. 5A shows the bone displacement device 200 in a ready state where the expandable member 250 is not expanded and a distal portion of the bone displacement device 200 is substantially straight. FIG. 5B shows the bone displacement device 200 in a cavity forming state where the expandable member 250 is expanded and the distal portion is articulated.

Figure 6:
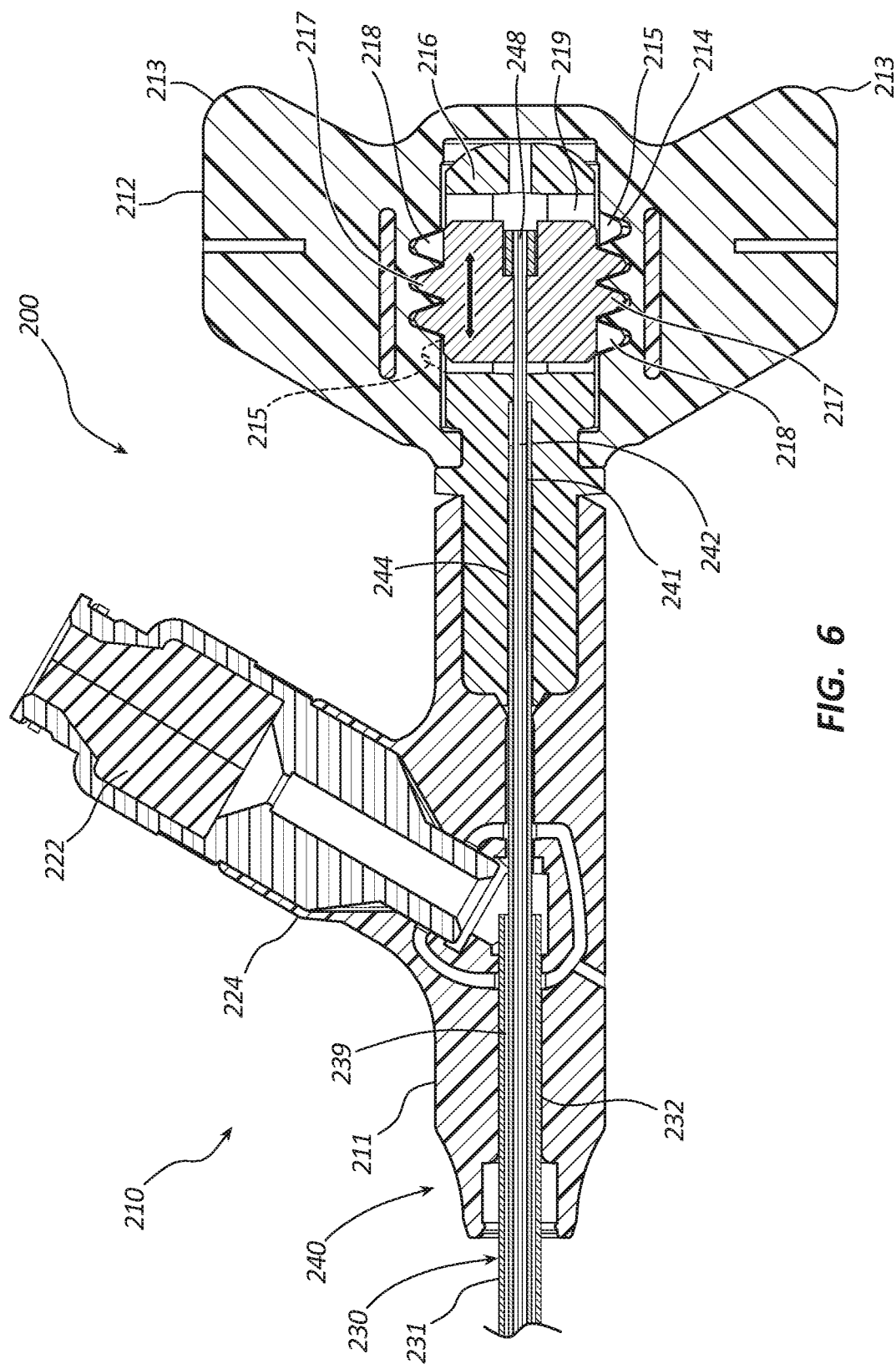
FIG. 6 is a longitudinal cross-sectional view of a proximal portion of the bone displacement device of FIG. 5A.

FIG. 6 illustrates a proximal portion of the bone displacement device 200. The proximal portion may comprise the handle 210, a proximal portion of the catheter 230, and a proximal portion of the stylet 240. The catheter 230 may comprise an elongate outer tube 231 having a proximal portion 232. A proximal end of the outer tube 231 can be fixedly coupled to the handle 210.

The stylet 240 is shown to comprise a tubular shaft 241 having a proximal portion 244. A proximal end of the shaft 241 may be fixedly coupled to the handle 210 at a location proximal of the proximal end of the outer tube 231. One or more pull wires 242 can be disposed within the shaft 241.

Figure 7:
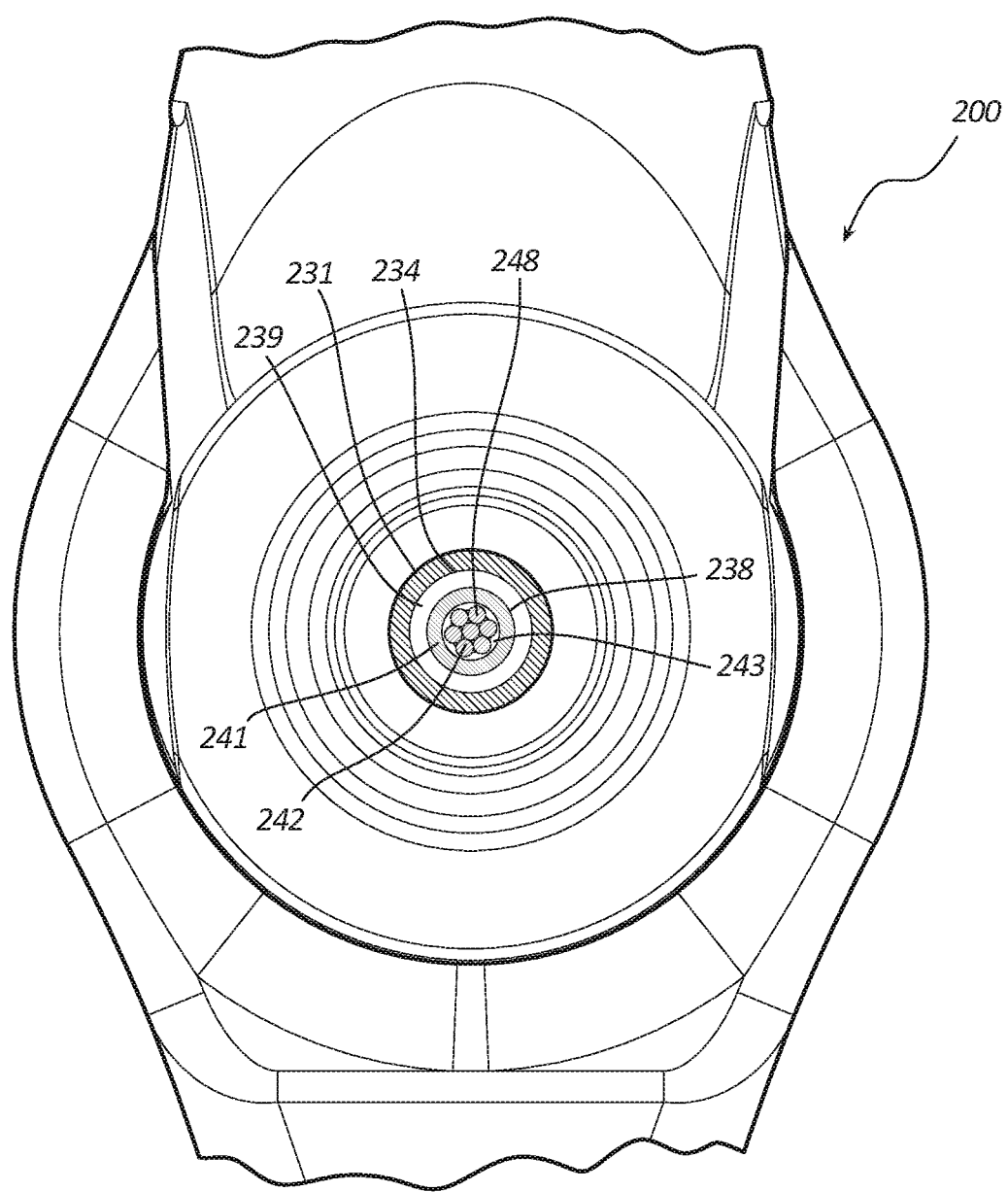
FIG. 7 is a transverse cross-sectional view of a middle portion of the bone displacement device of FIG. 5A.

FIG. 7 illustrates a transverse cross-section of a middle portion of the bone displacement device 200. As illustrated, the outer tube 231 includes an outer lumen 234. The shaft 241 may be coaxially disposed within the outer lumen 234. An annular space 239 may be formed between the outer tube 231 and the shaft 241. The shaft 241 may include a shaft lumen 243. The pull wires 242 can be disposed within the shaft lumen 243.

Referring again to FIG. 6, the handle 210 may comprise a body 211 and a rotatable grip 212 rotatably coupled to a proximal end of the body 211. The body 211 may comprise a side port 224 extending laterally from a longitudinal axis of the body 211. The side port 224 may be in fluid communication with the annular space (239 of FIG. 7). A fluid delivery device (e.g., syringe) can be releasably coupled to a proximal portion of the side port 224. A valve member 222 may be disposed within the side port 124. The valve member 222 may be configured to selectively permit air or fluid to be directed through the side port 224, through the annular space 239, and to the expandable member 250 when the fluid delivery device is coupled to the side port 224. The valve member 222 may also be configured to retain the air or fluid within the annular space 239 and the expandable member 250 when the fluid delivery device is removed from the side port 224.

In the illustrated embodiment, the proximal end of the outer tube 231 can be coupled to the body 211 at a location distal to the side port 224. The shaft 241 can be coupled to the body 211 at a location proximal to the outer tube 231.

The rotatable grip 212 may be configured to be rotatable around a longitudinal axis of the handle 210. The rotatable grip 212 may comprise generally laterally and proximally extending wings 213 configured to be gripped by a user. The rotatable grip 212 may comprise a chamber 219 configured to receive a pull member 216. The chamber 219 may include a female thread 214 configured to engage a male thread 217 of the pull member 216. The female thread 214 may comprise proximal and distal thread stops 215. The male thread 217 may comprise proximal and distal thread stops 218. The female thread stops 215 can be configured to engage with the male thread stops 218 to prevent over-rotation of the rotatable grip 212 in both a first direction and a second direction.

Figure 5B:
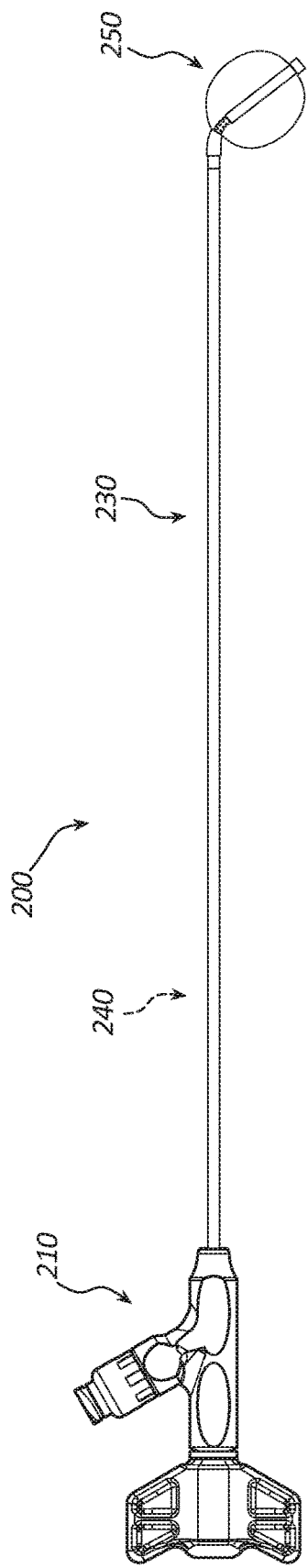
FIG. 5B is a side view of the bone displacement device of FIG. 5A in a bone displacement state.

In the illustrated embodiment, the proximal ends of the pull wires 242 may be fixedly coupled to the pull member 216. When the rotatable grip 212 is rotated in the first direction, the pull member 216 can be displaced proximally, causing a tension force to be applied to the pull wires 242. The tension force on the pull wires 242 may result in a tension force being applied to the distal end of the shaft 241 and articulation of the shaft 241 and the bone displacement device 200, as shown in FIG. 5B.

Rotation of the rotatable grip 212 in the second direction may displace the pull member 216 distally and release the tension force on the pull wires 242, resulting in the distal portion of the bone displacement device 200 returning to a substantially straight configuration, as shown in FIG. 5A. The rotatable grip 212 can be rotated in the second direction until the distal female thread stop 215 engages with the distal male thread stop 218.

FIGS. 8A-8B illustrate a distal portion of the bone displacement device 200. The distal portion may comprise an expandable member 250, a distal portion 233 of the outer tube 231, and a distal portion 245 of the shaft 241. The shaft 241 may extend beyond the distal end of the outer tube 231. In the illustrated embodiment, the expandable member 250 comprises a balloon 251.

The balloon 251 may comprise a balloon wall, such as a double balloon wall 252 configured to expand radially outward without stretching when air or fluid is injected into the balloon 251 through the annular space 239. A proximal portion of the balloon 251 may be sealingly coupled to the distal end of the outer tube 231. A tie layer 253 may be disposed between the balloon wall 252 and the outer tube 231 to facilitate bonding of the balloon wall 252 to the outer tube 231.

A distal portion of the balloon 251 may be sealingly coupled to a distal end of a tip tie tube 255. The tip tie tube 255 may extend proximally over the distal portion 245 of the shaft 241. The tip tie tube 255 and shaft 241 may configured in a "piston/cylinder" type arrangements where the shaft 214 is allowed to move with respect to the tip tie tube when the balloon 251 is inflated or deflated. For example, the tip tie tube 255 may be configured to piston proximally over the shaft 241 when the balloon 251 is inflated and to piston distally over the shaft 241 when the balloon 251 is deflated. A plug 254 may be sealingly disposed within the distal end of the tip tie tube 255.

The seal of the proximal end of the balloon 251 to the outer tube 231 and the seal of the distal end of the balloon 251 to the tip tie tube 255 may form a balloon chamber 256 configured to be pressurized. The balloon chamber 256 may be pressurized up to a pressure of about 60 atm. The balloon 251 may be expanded to a diameter of from about 10 mm to about 30 mm.

As shown in FIGS. 8A-8B, the distal portion of the shaft 241 may comprise a plurality of laser cuts 247. The laser cuts 247 may facilitate articulation of the shaft 241 when the tension force is applied to the pull wires 242, as shown in FIG. 8B.

Figure 9A:
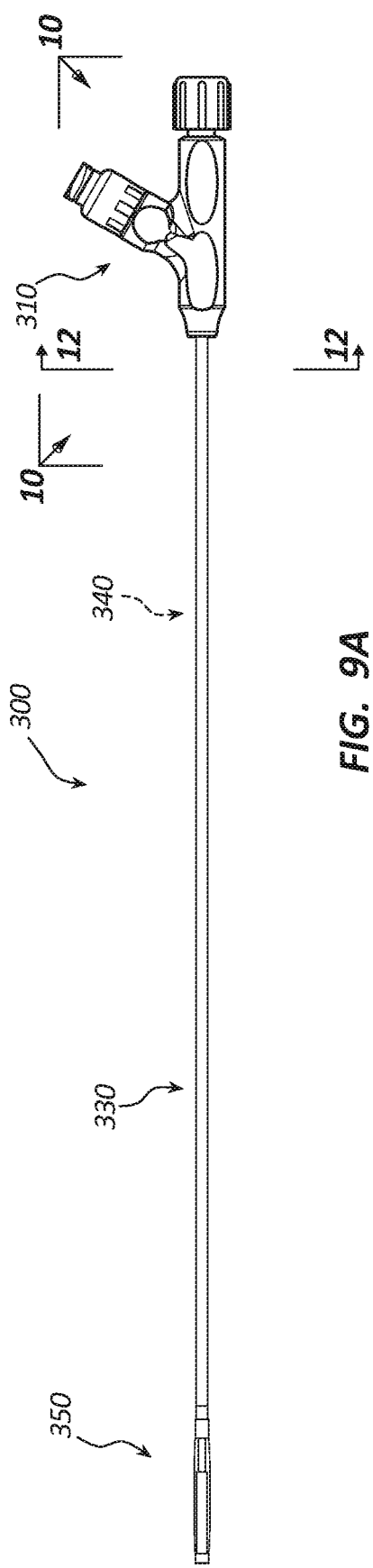
FIG. 9A is a side view of another embodiment of a bone displacement device in a ready state.
Figure 9B:
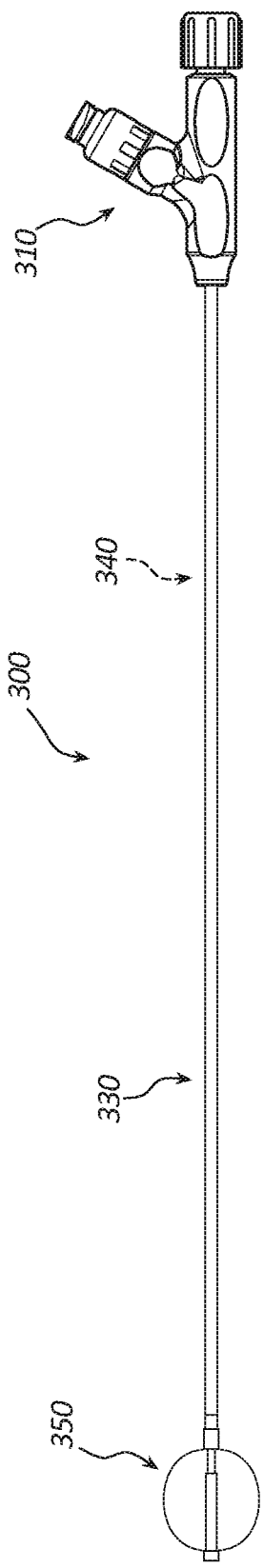
FIG. 9B is a side view of the bone displacement device of FIG. 9A in a bone displacement state.

FIGS. 9A-13B depict another embodiment of a bone displacement device 300. In the illustrated embodiment, the bone displacement device 300 is partially composed of a handle 310, a catheter 330, a stylet 340, and an expandable member 350. FIG. 9A shows the bone displacement device 300 in a ready state where the expandable member 350 is not expanded and a distal portion of the bone displacement device 300 is substantially straight. FIG. 9B shows the bone displacement device 300 in a cavity forming state where the expandable member 350 is expanded and the distal portion is substantially straight.

Figure 10:
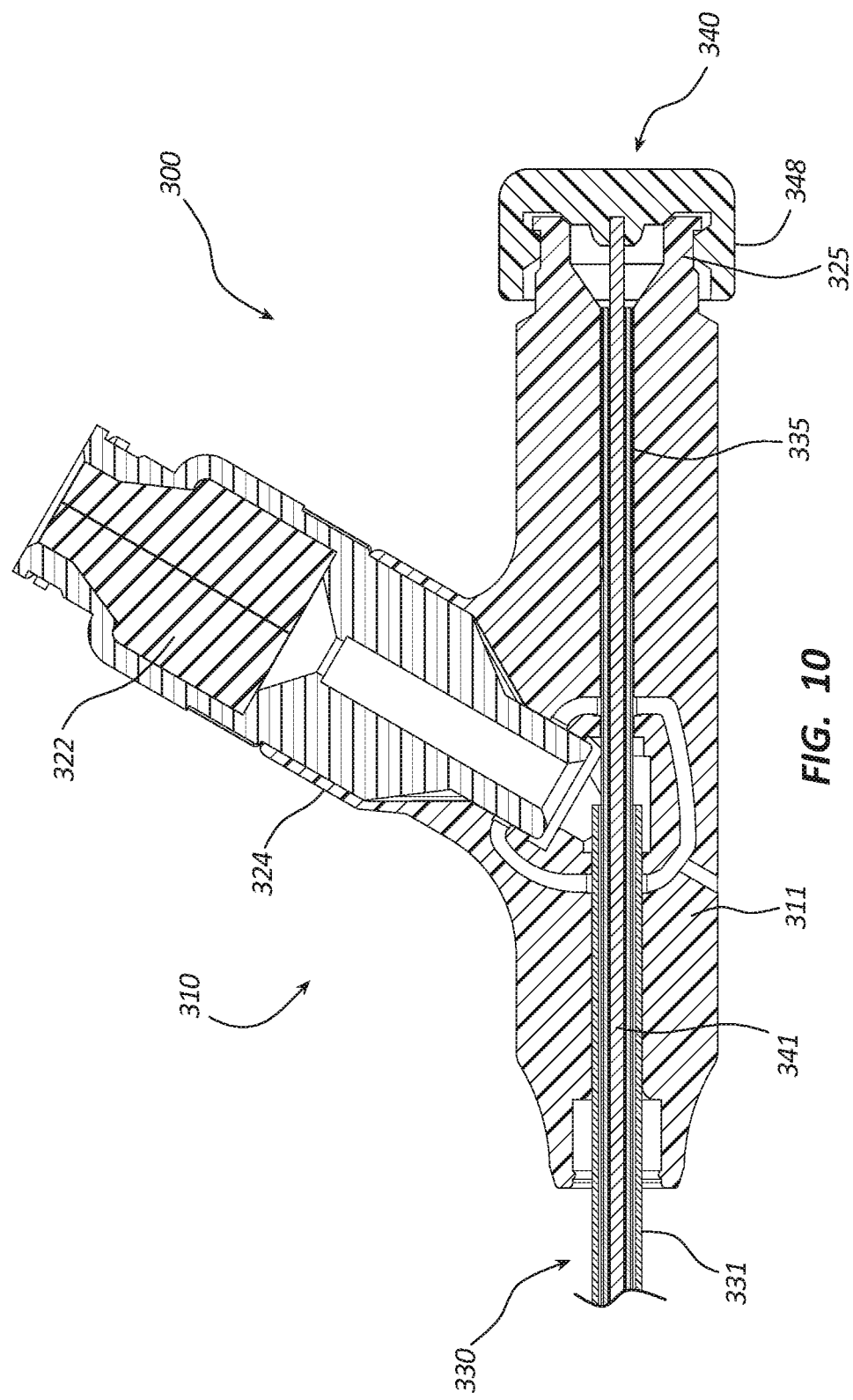
FIG. 10 is a cross-sectional view of a proximal portion of the bone displacement device of FIG. 9A.

FIG. 10 illustrates a proximal portion of the bone displacement device 300. The proximal portion may comprise the handle 310, a proximal portion of the catheter 330, and a proximal portion of the stylet 340. The catheter 330 may comprise an elongate outer tube 331 and an elongate inner tube 335. A proximal end of outer tube 331 can be coupled to the handle 310. The inner tube 335 may be coaxially disposed within the outer tube 331. A proximal end of the inner tube 335 can be coupled to the handle 310 at a location proximal of the proximal end of the outer tube 331.

The handle 310 may comprise a body 311. The body 311 may comprise a side port 324 extending laterally from a longitudinal axis of the body 311. The side port 324 may be in fluid communication with an annular space (339 of FIG. 12). A fluid delivery device (e.g., syringe) can be releasably coupled to a proximal portion of the side port 324. A valve member 322 may be disposed within the side port 324. The valve member 322 may be configured to selectively permit air or fluid to be directed through the side port 324, through the annular space 339, and to the expandable member 350 when the fluid delivery device is coupled to the side port 324. The valve member 322 may also be configured to retain the air or fluid within the annular space 339 and the expandable member 350 when the fluid delivery device is removed from the side port 324. The body 311 may include a proximal port 325 in fluid communication with the inner tube 335. The proximal port 325 may be configured to receive the stylet 340. In one embodiment, the proximal port 325 may include a female luer taper and a thread engagement feature.

In the illustrated embodiment, the proximal end of the outer tube 331 can be coupled to the body 311 at a location distal to the side port 324. The inner tube 335 can be coupled to the body 311 at a location proximal to the outer tube 331.

Figure 11:
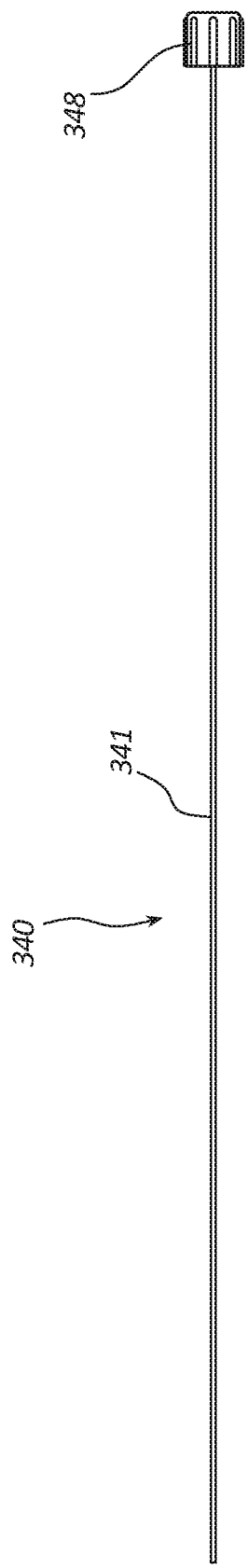
FIG. 11 is a side view of a stylet of the bone displacement device of FIG. 9A.

FIG. 11 depicts the stylet 340. The stylet 340 may comprise a shaft 341 and a connector 348. The shaft 341 may be a cylindrical rod. In other embodiments, the shaft 341 may be a cylindrical tube. A proximal end of the shaft 341 may be fixedly coupled to the connector 348. In the illustrated embodiment, the connector 348 is a male luer nut. The connector 348 may be configured to be removably coupled to the proximal port 325 such that the stylet 340 may be inserted into and removed from the bone displacement device 300 through the proximal port 325.

Figure 12:
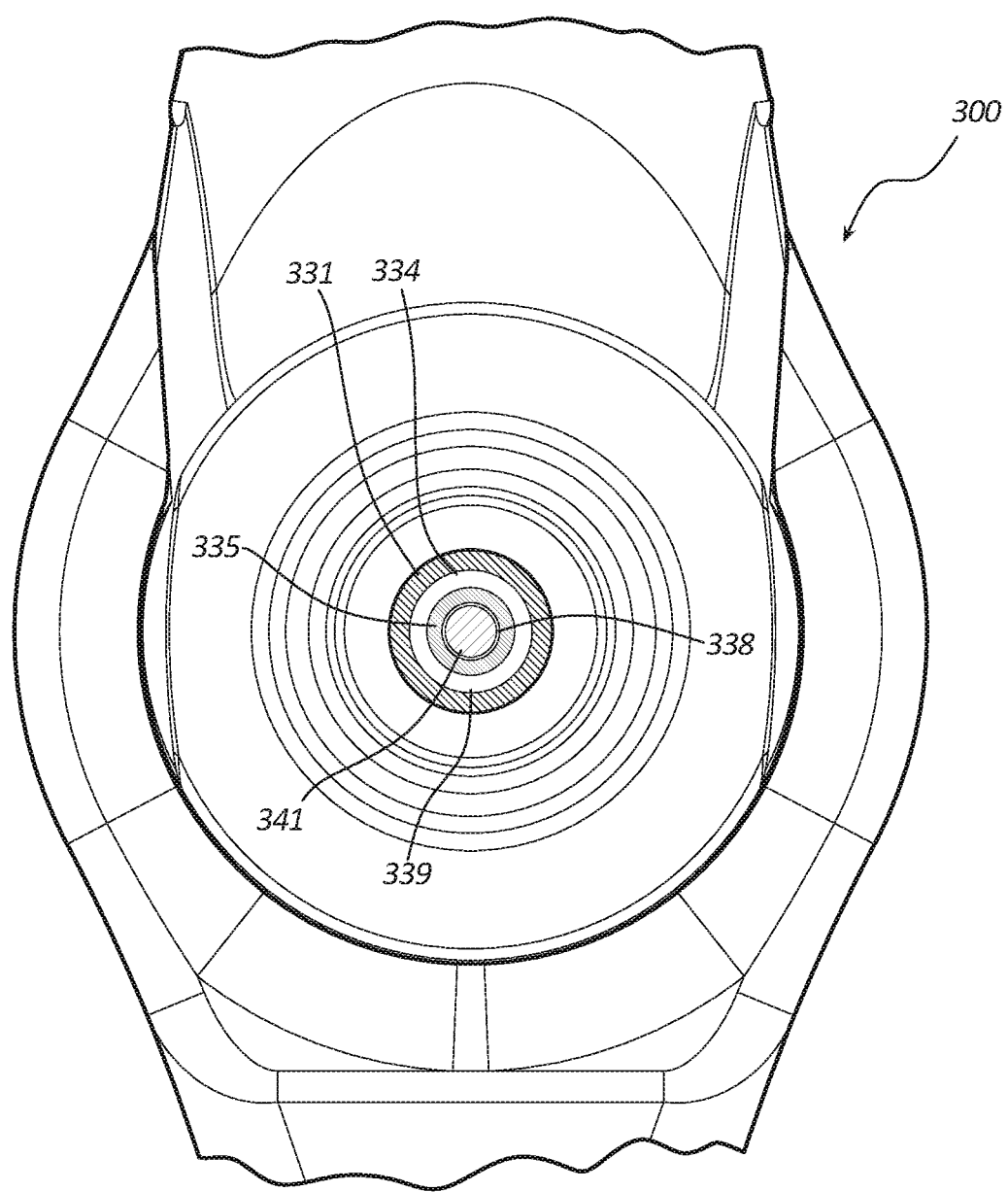
FIG. 12 is a transverse cross-sectional view of a middle portion of the bone displacement device of FIG. 9A.

FIG. 12 illustrates a transverse cross-section of a middle portion of the bone displacement device 300. As illustrated, the outer tube 331 includes an outer lumen 334. The inner tube 335 is shown to be coaxially disposed within the outer lumen 334. An annular space 339 may be defined between the outer tube 331 and the inner tube 335. The inner tube may include an inner lumen 338. The shaft 341 may be coaxially disposed within the inner lumen 338.

FIGS. 13A-13B illustrate a distal portion of the bone displacement device 300. The distal portion may comprise an expandable member 350, a distal portion 333 of the outer tube 331, a distal portion 337 of the inner tube 335, and a distal portion 345 of the shaft 341. The inner tube 335 and the shaft 341 may extend beyond the distal end of the outer tube 331. The inner tube 335 may extend beyond the distal end of the shaft 341. In the illustrated embodiment, the expandable member 350 comprises a balloon 351.

A proximal portion of the balloon 351 may be sealingly coupled to the distal end of the outer tube 331. A tie layer 353 may be disposed between a balloon wall 352 and the outer tube 331 to facilitate bonding of the balloon wall 352 to the outer tube 331. A distal portion of the balloon 351 may be sealingly coupled to the distal end of the inner tube 335. A tip tie tube 355 may be disposed between the balloon wall 352 and the inner tube 335. The tip tie tube 355 may extend proximally over the distal portion 337 of the inner tube 335 and the distal portion 345 of the shaft 341. The tip tie tube 355 and shaft 341 may be configured to move in a piston/cylinder configuration when the balloon 351 is inflated and deflated. For example the tip tie tube 335 may move proximally over the shaft 341 when the balloon 351 is inflated, as shown in FIG. 13A, and to piston distally over the shaft 341 when the balloon 351 is deflated, as shown in FIG. 13B.

Figure 14A:
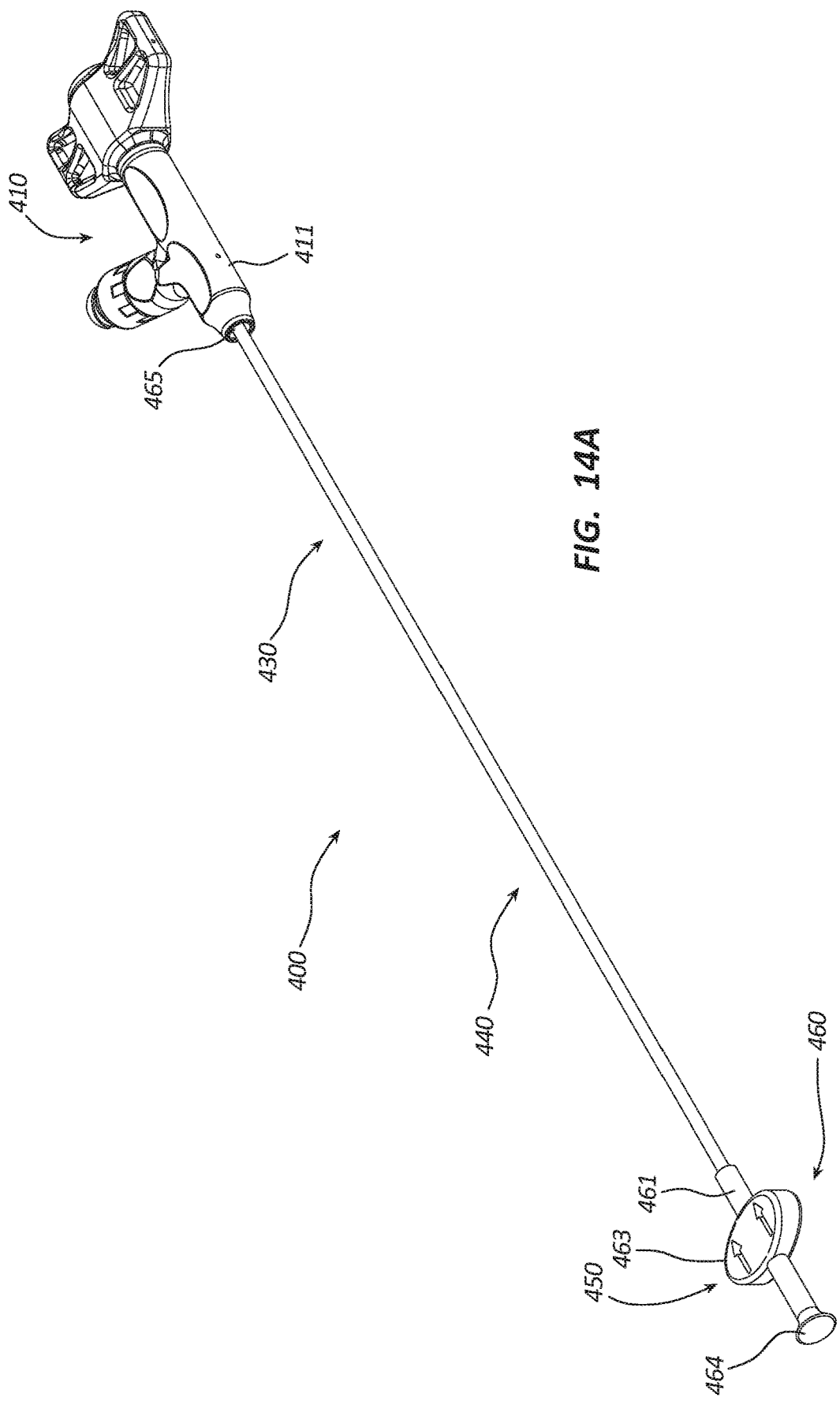
FIG. 14A is a side view of another embodiment of a bone displacement device in a package state.
Figure 14B:
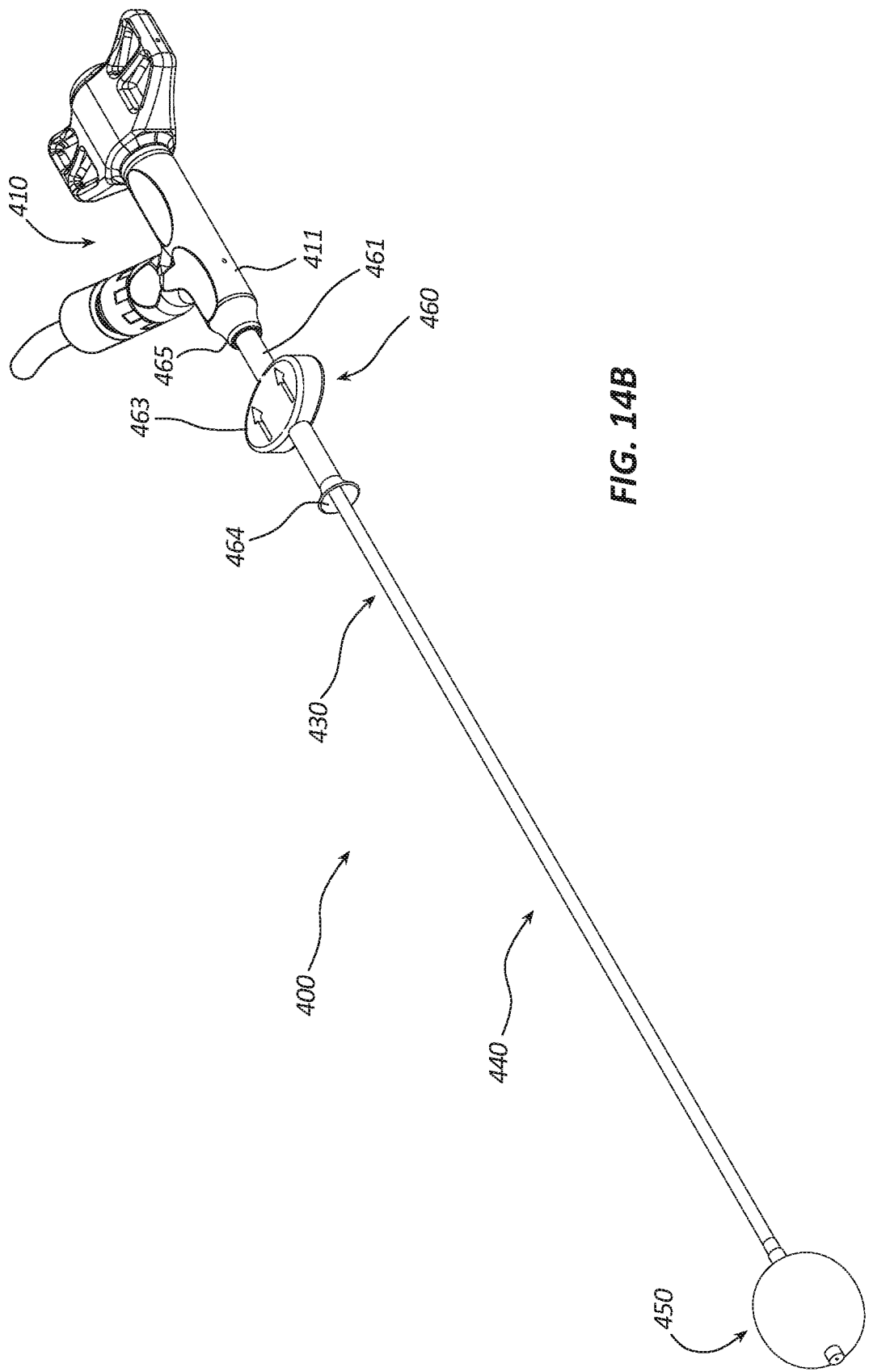
FIG. 14B is a side view of the bone displacement device of FIG. 14A in a ready state.

FIGS. 14A-14B depict another embodiment of a bone displacement device 400. In the illustrated embodiment, the bone displacement device 400 comprises a handle 410, a catheter 430, a stylet 440, an expandable member 450, and a protective sleeve 460. FIG. 14A shows the bone displacement device 400 in a package state where the protective sleeve 460 surrounds the expandable member 450. FIG. 14B shows the bone displacement device 400 in a ready state where the protective sleeve 460 is displaced proximally over the catheter 430 and releasably coupled to the handle 410.

In the depicted embodiment, the protective sleeve 460 may include a tubular body 461 and a grip 463 coupled to the tubular body 461. A distal end 464 of the tubular body 461 may be formed in a funnel shape to facilitate passage of the protective sleeve 460 distally over the expandable member 450 when not expanded. A proximal end of the tubular body 461 may be sized to be releasably received into a recess 465 disposed at a distal end of a body 411 of the handle 410, as shown in FIG. 14B. In other embodiments, the proximal end of the tubular body 461 may be sized to fit over a protrusion extending from the distal end of the body 411.

As depicted in the illustrated embodiment, the grip 463 has an oval shape. In other embodiments, the grip 463 may have any suitable shape that is grippable with fingers of a user. For example, the grip 463 may have a rectangular, square, circular, or triangular shape, etc. In some embodiments, the grip 463 may include grip enhancing features, such as ridges, bumps, recesses, etc. In another embodiment, the grip 463 may include indicia (e.g., an arrow) to indicate the direction the protective sleeve 460 could be moved prior to use of the bone displacement device 400.

The protective sleeve 460 may be disposed over the expandable member 450 during a manufacturing assembly of and prior to packaging of the bone displacement device 400. In preparation for a treatment procedure, a user can remove the bone displacement device 400 from its package in the package state, as shown in FIG. 14A, where the protective sleeve 460 is disposed over the expandable member 450. The user may then proximally displace the protective sleeve 460 and releaseably couple the protective sleeve 460 to the handle 410, as shown in FIG. 14B, prior to insertion of the bone displacement device 400 into a vertebral bone of a patient to prevent the protective sleeve 460 from inadvertent distal displacement into a working field. In some procedures, upon removal of the bone displacement device 400 from the vertebral bone, the user may longitudinally distally displace the protective sleeve 460 to rewrap (e.g., radially compress) the expandable member 450 in preparation for re-insertion of the bone displacement device 400.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A bone displacement device, comprising:
   an elongate outer tube;
   an elongate stylet coaxially disposed within the outer tube, wherein the stylet comprises a tubular shaft and a plurality of pull wires disposed within a lumen of the shaft, the plurality of pull wires are configured to be pulled proximally;
   a handle coupled to a proximal portion of the outer tube and the stylet, wherein the handle comprises a rotatable grip, wherein the plurality of pull wires are coupled to a pull member disposed within the rotatable grip, and wherein the rotatable grip engages with threads of the pull member to displace the pull member proximally and distally;
   an expandable member disposed adjacent a distal end of the outer tube; and
   a tip tie tube disposed within the expandable member and coupled to a distal end of the expandable member and slidably disposed over a distal portion of the stylet, wherein the tip tie tube is displaced proximally relative to the distal portion of the stylet when the expandable member is expanded, and is displaced distally relative to the distal portion of the stylet when the expandable member is contracted.

2. The bone displacement device of claim 1, wherein the stylet comprises seven pull wires, with a central pull wire and the other six pull wires equally spaced around the central pull wire.

3. The bone displacement device of claim 1, wherein the plurality of pull wires are coupled to a proximal end of the pull member.

4. The bone displacement device of claim 3, wherein the pull member comprises male threads configured to engage with female threads of the rotatable grip.

5. The bone displacement device of claim 3, wherein the pull member is displaced proximally when the rotatable grip is rotated in a first direction to apply a tension force to the plurality of pull wires, and displaced distally when the rotatable grip is rotated in a second direction to release the tension force from the plurality of pull wires, and wherein a distal portion of the stylet articulates when the tension force is applied to the plurality of pull wires.

6. The bone displacement device of claim 4, wherein the male threads comprise a proximal male thread stop and a distal male thread stop;
   wherein the female threads comprise a proximal female thread stop and a distal female thread stop;
   wherein the proximal male thread stop is configured to engage with the proximal female thread stop to limit proximal displacement of the pull member; and
   wherein the distal male thread stop is configured to engage with the distal female thread stop to limit distal displacement of the pull member.

7. The bone displacement device of claim 1, wherein the tip tie tube comprises a braided material.

8. The bone displacement device of claim 1, further comprising an elongate inner tube coaxially disposed between the outer tube and the stylet.

9. The bone displacement device of claim 8, wherein a proximal portion of the expandable member is sealingly coupled to a tie layer, and the tie layer is sealingly coupled to a distal portion of the outer tube, and wherein a distal portion of the expandable member is sealingly coupled to the tip tie tube, and the tip tie tube is sealingly coupled to a distal portion of the inner tube.

10. The bone displacement device of claim 1, wherein the expandable member is a balloon.

11. The bone displacement device of claim 1, wherein the handle comprises a side port and a valve member disposed within the side port.

12. A bone displacement system, comprising:
   a bone displacement device, comprising:
      an elongate outer tube;
      an elongate stylet coaxially disposed within the outer tube, wherein the stylet comprises a tubular shaft and a plurality of pull wires disposed within a lumen of the shaft, the plurality of pull wires are configured to be pulled proximally;
      a handle coupled to a proximal end of the outer tube and the stylet, wherein the handle comprises a rotatable grip, wherein the plurality of pull wires are coupled to a pull member disposed within the rotatable grip, and wherein the rotatable grip engages with threads of the pull member to displace the pull member proximally or distally;

an expandable member disposed adjacent a distal end of the outer tube; and a tip tie tube disposed within the expandable member and coupled to a distal end of the expandable member and slidably disposed over a distal portion of the stylet, wherein the tip tie tube is displaced proximally relative to the distal portion of the stylet when the expandable member is expanded, and is displaced distally relative to the distal portion of the stylet when the expandable member is contracted; and a protective sleeve configured to be slidably displaceable over the outer tube.

13. The bone displacement system of claim 12, wherein the stylet comprises seven pull wires.

14. A method of displacing bone, comprising:

obtaining a bone displacement device, comprising:

an elongate outer tube;

an elongate stylet coaxially disposed within the outer tube, wherein the stylet comprises a tubular shaft and a plurality of pull wires disposed within a lumen of the shaft, the plurality of pull wires are configured to be pulled proximally;

a handle coupled to a proximal end of the outer tube and the stylet, wherein the handle comprises a rotatable grip, wherein the plurality of pull wires are coupled to a pull member disposed within the rotatable grip, and wherein the rotatable grip engages with threads of the pull member to displace the pull member proximally or distally;

an expandable member disposed adjacent a distal end of the outer tube; and a tip tie tube disposed within the expandable member and coupled to a distal end of the expandable member and slidably disposed over a distal portion of the stylet, wherein the tip tie tube is displaced proximally relative to the distal portion of the stylet when the expandable member is expanded, and is displaced distally relative to the distal portion of the stylet when the expandable member is contracted;

inserting a distal portion of the bone displacement device into a bone;

articulating a distal portion of the stylet; and expanding the expandable member.

15. The method of claim 14, wherein articulating the distal portion of the stylet further comprises rotating the rotatable grip in a first direction, wherein a tension force is applied to the plurality of pull wires.

16. The method of claim 14, wherein the bone displacement device further comprises a protective sleeve.

17. The method of claim 16, further comprising displacing the protective sleeve proximally from a bone displacement device package state where the protective sleeve surrounds the expandable member to a bone displacement device ready state where the protective sleeve is coupled to the handle.

18. The bone displacement device of claim 1, wherein the pull member is displaced along a longitudinal axis of the device.

19. The bone displacement device of claim 3, wherein the proximal end of the pull member is distal a proximal end of the rotatable grip.

20. The bone displacement device of claim 1, further comprising a plug sealingly disposed within a distal end of the tip tie tube.

21. The bone displacement system of claim 12, further comprising a plug sealingly disposed within a distal end of the tip tie tube.

22. The method of claim 14, wherein the bone displacement device further comprises a plug sealingly disposed within a distal end of the tip tie tube.

* * * * *